United States Patent [19]

Carini et al.

[11] Patent Number: 5,210,079

[45] Date of Patent: May 11, 1993

[54] TREATMENT OF CHRONIC RENAL FAILURE WITH IMIDAZOLE ANGIOTENSIN-II RECEPTOR ANTAGONISTS

[75] Inventors: David J. Carini, Wilmington; John Jonas V. Duncia, Newark; Pancras C. Wong, Wilmington, all of Del.

[73] Assignee: E. I. Du Pont de Nemours and Company, Wilmington, Del.

[21] Appl. No.: 832,638

[22] Filed: Feb. 7, 1992

Related U.S. Application Data

[63] Continuation of Ser. No. 542,351, Jun. 22, 1990, abandoned, which is a continuation-in-part of Ser. No. 279,194, Dec. 6, 1988, Pat. No. 5,138,069, which is a continuation-in-part of Ser. No. 142,580, Jan. 7, 1988, abandoned, which is a continuation-in-part of Ser. No. 373,755, Jun. 30, 1989, abandoned.

[51] Int. Cl.$^5$ .............. A61K 31/41; A61K 31/44; A61K 31/64; A61K 31/415
[52] U.S. Cl. ...................... 514/94; 514/256; 514/279; 514/359; 514/381; 514/385
[58] Field of Search .............. 514/94, 256, 279, 359, 514/381, 385

[56] References Cited

U.S. PATENT DOCUMENTS

| | | | |
|---|---|---|---|
| 3,772,315 | 11/1973 | Regel et al. | 260/296 R |
| 4,207,324 | 6/1980 | Matsumura et al. | 424/273 R |
| 4,226,878 | 10/1980 | Izuka | 424/273 R |
| 4,301,169 | 11/1981 | Yamanaka et al. | 424/273 R |
| 4,328,349 | 5/1982 | Grayboyes et al. | 548/343 |
| 4,340,598 | 7/1982 | Furukawa et al. | 424/273 R |
| 4,347,364 | 8/1982 | Walser et al. | 546/256 |
| 4,347,365 | 8/1982 | Walser et al. | 546/256 |
| 4,355,040 | 11/1982 | Furukawa et al. | 424/273 R |
| 4,379,927 | 4/1983 | Vorbruggen et al. | 544/139 |
| 4,402,966 | 9/1983 | Yamanaka et al. | 424/273 R |
| 4,448,781 | 5/1984 | Cross et al. | 424/269 |
| 4,463,011 | 7/1984 | Ogata et al. | 424/273 |
| 4,533,669 | 8/1985 | Yamanaka et al. | 514/396 |
| 4,602,031 | 7/1986 | Yamanaka et al. | 514/399 |

FOREIGN PATENT DOCUMENTS

| | | |
|---|---|---|
| 0028834 | 5/1981 | European Pat. Off. . |
| 0103647 | 3/1984 | European Pat. Off. . |
| 0125033A | 11/1984 | European Pat. Off. . |
| 0142754 | 5/1985 | European Pat. Off. . |
| 0146228 | 6/1985 | European Pat. Off. . |
| 0160307 | 11/1985 | European Pat. Off. .......... 7/5 |
| 0253310 | 1/1988 | European Pat. Off. . |
| 0323841 | 7/1989 | European Pat. Off. . |
| 0324377 | 7/1989 | European Pat. Off. . |
| 0403159 | 12/1990 | European Pat. Off. . |
| 0437103 | 7/1991 | European Pat. Off. . |
| 2946020 | 5/1980 | Fed. Rep. of Germany . |
| 3426081 | 1/1986 | Fed. Rep. of Germany . |
| 3426195 | 1/1986 | Fed. Rep. of Germany . |
| 57-98270 | 6/1982 | Japan . |
| WO9100277 | 1/1991 | PCT Int'l Appl. . |

OTHER PUBLICATIONS

Pals, et al. 1971, Circ. Res. 29:673–681. "Role of the Pressor Action . . . ".
Zatz, et al. 1985, Proc. Nat. Acad. Sci. 82:5963–5967. "Predominance. . . ".
Anderson, et al. 1985, J. Clin. Invest. 76:612–619, "Control of . . . ".
Anderson & Brenner Hypertension: Pathophysiology, Diagnosis & Management Chapt. 72: pp. 1163–1176 (1990).
Wong, et al., Pharmacol. Exp. Ther., 215:104, 1980.
Dunn, Hospital Practice, 19:99, 1984.
Dzau, et al., N. Eng. J. Med., 310:347, 1984.

Primary Examiner—S. J. Friedman

[57] ABSTRACT

Substituted imidazoles such as 2-butyl-4-chloro-1-[(2'-(1H-tetrazol-5-yl)biphenyl-4-yl)methyl]-5-(hydroxymethyl)imidazole and 2-butyl-4-chloro-1-[(2'-carboxybiphenyl-4-yl)-methyl]-5-(hydroxymethyl)imidazole and pharmaceutically acceptable salts thereof are useful for treating chronic renal failure, mediated by angiotensin-II.

31 Claims, No Drawings

OTHER PUBLICATIONS

Lindgren, et al., *Eur. J. Pharmacol., 135:383, 1987.*
Zatz, et al., *Kidney International*, vol. 31, Suppl. 20, pp. S-123-129 (1987).
Schmidt et al., J. Cardiovascular Pharmacology, vol. 8, pp. S100-105 (1986).
Wong et al., *Life Sciences,* 27:1291-1297 (1980).
Anderson et al., *Hypertension: Pathophysiology, Diagnosis, and Management,* Chapter 73, pp. 1163-1176 (1990).
Anderson et al., *Hypertension: Pathophysiology, Diagnosis, and Management, Chapter 104, pp. 1677-1687 (1990).*
Torii, H., Takeda Kenkyushoho, 41, No. 3/4, 180-191, (1982).
Streeten et al., *Handbook of Hypertension,* vol. 5, pp. 246-247, (1984).
Keeton, T. K. et al., *Pharmacol. Rev., vol. 31, pp. 81-227, (1981).*
Weinberger, M. H. et al., *Medical Clinics N. America,* vol. 71, (1987).
Dunn, M. J., *Hospital Practice,* vol. 19, pp. 99-113 (1984).
Satoh et al., *Circ. Res.*, 36/37 (Suppl. I):I-89 to 1-96 (1975).
Blasingham et al., *Am. J. Physiol.,* vol. 2339, F360, (1980).
Wong et al., *J. Pharmacol. Exp. Therm., vol. 219, pp. 104-109 (1980).*
Raij et al., *Journal of Hypertension Supplement,* vol. 7, Suppl. 7, pp. S33-S37 (Sep. 1989).
Abdulkader et al., *Brazilian Journal of Medical and Biological Research,* 21 (2):233-239 (1988).
Magnusson et al., *Kidney International Supplement* 16, vol. 24, pp. S324-S326 (Dec. 1983).

Huland et al., *Transplantation,* 36(2):139-142 (Aug. 1983).
Mento et al., *J. Cardiovascular Pharmacol.,* 8(4):670-675 (1986).
MacDonald et al., *Kidney International,* 31 (S20):S148-S153 (1987).
Anderson et al,, *Am. J. Hypertens.* 4(5): 11a-12A (1991).
Lafayette et al., *Am. Soc. Nephrology,* 23d. Ann. Mtg. (Dec. 2-5, 1990).
Hutchinson et al., *Clinical Research*, vol. 539, No. 2, p. 358A (1991).
H. Torii, *Takeda Kenkyushoho,* 40, No. 3/4, 180-191 (1982).
Streeten and Anderson, Handbook of Hypertension, vol. 5, Clinical Pharmacology of Antihypertensive Drugs, A. E. Doyle (Editor), Elsevier Science Publishers B. V., p. 246 (1984).
Satoh, et al., *Cir. Res.* 36/37 & Suppl. I):I-89, 1975.
Blasingham et al., Am. J. Physiol. 239:F360, 1980.
Wong et al., Abstract No. 30, *Hypertension*, p. 340. vol. 12, No. 3, Sep. 1988 High Blood Pressure Council Mtg., San Francisco, Calif., Sep. 28-Oct. 1, 1988, "X-6803 Methyl 2-N-Butyl-1-(4-(2-Carboxybenzamido) Benzyl-4-Chloroimidazole-5-Acetate, Sodium Salt): A Novel Nonpeptide Angiotension II Receptor Antagonist".
Chiu et al., Abstract No. 118.11, *The Pharmacologist*, vol. 30, p. A165, 1988, for ASPET mtg., Montreal, Canada, Oct. 9-13, 1988: "Nonpeptide Angiotensin II (AII) Receptor Antagonists: Structure Function Studies".
Wong et al., Nonpeptide Angiotensin II Receptor Antognists. I. Pharmacological Characterization of 2-n-Butyl-chloro-1-(2-chlorobenzyl)imidazole-5-acetic acid, sodium salt (S-8307), "J. Pharmacology and Experimental Therapeutics, "vol. 247, No. 1, pp. 1-7.

TREATMENT OF CHRONIC RENAL FAILURE WITH IMIDAZOLE ANGIOTENSIN-II RECEPTOR ANTAGONISTS

CROSS REFERENCE TO RELATED APPLICATIONS

This is a continuation of application U.S. Ser. No. 07/542,351 filed Jun. 22, 1990, now abandoned, which is a continuation-in-part of U.S. Ser. No. 279,194 filed Dec. 6, 1988, now U.S. Pat. No. 5,138,069, which is a continuation-in-part of U.S. Ser. No. 142,580 filed Jan. 7, 1988, now abandoned, which is a continuation-in-part of U.S. Ser. No. 373,755 filed on Jun. 30, 1989, now abandoned.

FIELD OF THE INVENTION

This invention relates to a method of treating chronic renal failure and, in particular, to a method which utilizes imidazole angiotensin-II (AII) receptor antagonists to treat chronic renal failure mediated by angiotensin-II.

BACKGROUND OF THE INVENTION

Angiotensin converting enzyme inhibitors may have beneficial effects over other antihypertensive agents in progressive renal disease of various origins including diabetic nephropathy, essential hypertension and other intrinsic renal diseases (See, e.g., Hypertension: Pathophysiology, Diagnosis, and Management, ed. by J. H. Laragh and B. M. Brenner, vol. 1, pp. 1163–1176, Raven Press, Ltd., New York, 1990; Hypertension: Pathophysiology, Diagnosis, and Management, ed. by J. H. Laragh and B. M. Brenner, vol. 2, pp. 1677–1687, Raven Press, Ltd., New York, 1990). For instance, in partially nephrectomized rats, glomerular capillary hypertension in the remnant kidney is associated with progressive proteinuria, focal glomerular sclerosis, and moderate hypertension. Angiotensin converting enzyme inhibitors, which lower systemic arterial pressure and glomerular capillary pressure, limit the progression of glomerular injury.

There are other antihypertensive agents which lower systemic arterial blood pressure to a similar extent, but fail to reduce glomerular capillary pressure. Such agents do not prevent the progression of glomerular injury. It is speculated that in these rats intrarenal generation of angiotensin-II constricts the renal efferent arteriole and causes an increase in glomerular hydraulic pressure. Glomerular hyperfiltration, hyperperfusion and/or hypertension may then initiate and induce glomerular lesions. Thus, blockade of the intrarenal formation of angiotensin-II by angiotensin converting enzyme inhibitors may retard the deterioration of renal failure.

Although the partially nephrectomized rat is associated with moderate hypertension, systemic hypertension does not appear to be necessary for the acceleration of renal disease. In the insulin-treated rat with streptozocin-induced diabetes, systemic arterial pressure is normal but glomerular capillary pressure is high. Similar to the partially nephrectomized rat model, angiotensin converting enzyme inhibitors are beneficial in limiting the glomerular structural lesions, suggesting that glomerular capillary hypertension but not systemic arterial hypertension play a critical role in rats with progressive renal failure.

Nonpeptide angiotensin-II receptor antagonists are believed to be more efficacious than angiotensin converting enzyme inhibitors in treating chronic renal failure because the nonpeptide angiotensin-II receptor antagonists may block the renal effect of angiotensin-II more completely irrespective of the source of angiotensin-II. In contrast, angiotensin converting enzyme inhibitors selectively block kininase II and, thus, may not inhibit totally the local formation of angiotensin-II in the kidney. Other types of peptidyl dipeptidase may also be responsible for the formation of angiotensin-II. (Wong, P. C. and Zimmerman, B. G.: Role of Extrarenal and Intrarenal Converting Enzyme Inhibition in Renal Vasodilator Response to Intravenous Captopril. Life Sci. 27: 1291, 1980; Schmidt M., Giesen-Crouse, E. M., Krieger, J. P., Welsch, C. and Imbs, J. L.: Effect of angiotensin converting enzyme inhibitors on the vasoconstrictor action of angiotensin I on isolated rat kidney. J. Cardiovasc. Pharmacol. 8 (Suppl. 10): S100, 1986)).

In clinical renal artery stenosis, the usefulness of angiotensin converting enzyme inhibitors may be limited by a reversible loss of filtration in the stenotic kidney. It is possible that nonpeptide angiotensin II receptor antagonists may have a similar renal effect in the stenotic kidney.

K. Matsumura, et al., in U.S. Pat. No. 4,207,324 issued Jun. 10, 1980 discloses 1,2-disubstituted-4-haloimidazole-5-acetic acid derivatives of the formula:

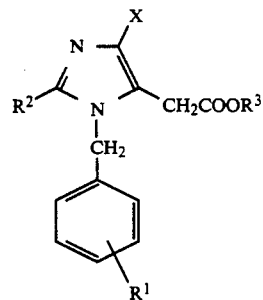

wherein $R^1$ is hydrogen, nitro or amino; $R^2$ is phenyl, furyl or thienyl optionally substituted by halogen, lower alkyl, lower alkoxy or di-lower alkylamino; $R^3$ is hydrogen or lower alkyl and X is halogen; and their physiologically acceptable salts. These compounds have diuretic and hypotensive actions.

Furukawa, et al., in U.S. Pat. No. 4,355,040 issued Oct. 19, 1982 discloses hypotensive imidazole-5-acetic acid derivatives having the formula:

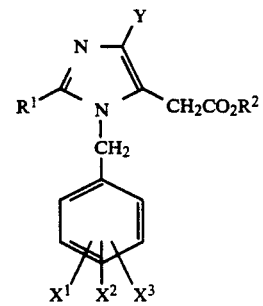

wherein $R^1$ is lower alkyl, cycloalkyl, or phenyl optionally substituted; $X^1$, $X^2$, and $X^3$ are each hydrogen, halogen, nitro, amino, lower alkyl, lower alkoxy, benzyloxy, or hydroxy; Y is halogen and $R^2$ is hydrogen or lower alkyl; and salts thereof.

Furukawa, et al., in U.S. Pat. No. 4,340,598, issued Jul. 20, 1982, discloses hypotensive imidazole derivatives of the formula:

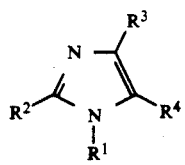

wherein $R^1$ is lower alkyl or, phenyl $C_{1-2}$ alkyl optionally substituted with halogen or nitro; $R^2$ is lower alkyl, cycloalkyl or phenyl optionally substituted; one of $R^3$ and $R^4$ is $-(CH_2)_nCOR^5$ where $R^5$ is amino, lower alkoxyl or hydroxyl and n is 0, 1, 2 and the other of $R^3$ and $R^4$ is hydrogen or halogen; provided that $R^1$ is lower alkyl or phenethyl when $R^3$ is hydrogen, n=1 and $R^5$ is lower alkoxyl or hydroxyl; and salts thereof.

Furukawa et al., in European Patent Application 103,647 discloses 4-chloro-2-phenylimidazole-5-acetic acid derivatives useful for treating edema and hypertension of the formula:

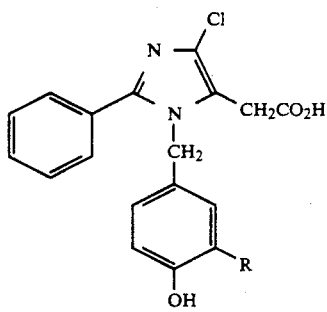

where R represents lower alkyl and salts thereof.

The metabolism and disposition of hypotensive agent 4-chloro-1-(4-methoxy-3-methylbenzyl)-2-phenyl-imidazole-5-acetic acid is discloses by H. Torii in Takeda Kenkyushoho, 41, No 3/4, 180–191 (1982).

Frazee et al., in European Patent Application 125,033-A discloses 1-phenyl(alkyl)-2-(alkyl)-thioimidazole derivatives which are inhibitors of dopamine-$\beta$-hydroxylase and are useful as antihypertensives, diuretics and cardiotonics. European Patent Application 146,228 filed Oct. 16, 1984 by S. S. L. Parhi discloses a process for the preparation of 1-substituted-5-hydroxymethyl-2-mercaptoimidazoles.

A number of references disclose 1-benzyl-imidazoles such as U.S. Pat. No. 4,448,781 to Cross and Dickinson (issued May 15, 1984); U.S. Pat. No. 4,226,878 to Ilzuka et al. (issued Oct. 7, 1980); U.S. Pat. No. 3,772,315 to Regel et al. (issued Nov. 13, 1973); U.S. Pat. No. 4,379,927 to Vorbrüggen et al. (issued Apr. 12, 1983); amongst others.

Pals et al., Circulation Research, 29, 673 (1971) describe the introduction of a sarcosin residue in position 1 and alanine in position 8 of the endogenous vasoconstrictor hormone AII to yield an (octa)peptide that blocks the effects of AII on the blood pressure of pithed rats. This analog, [$Sar^1$, $Ala^8$] AII, initially called "P-113" and subsequently "Saralasin", was found to be one of the most potent competitive antagonists of the actions of AII, although, like most of the so-called peptide-AII-antagonists, it also possesses agonistic actions of its own. Saralasin has been demonstrated to lower arterial pressure in mammals and man when the (elevated) pressure is dependent on circulating AII (Pals et al., Circulation Research, 29, 673 (1971); Streeten and Anderson, Handbook of Hypertension, Vol. 5, Clinical Pharmacology of Antihypertensive Drugs, A. E. Doyle (Editor), Elsevier Science Publishers B. V., p. 246 (1984)). However, due to its agonistic character, saralasin generally elicits pressor effects when the pressure is not sustained by AII. Being a peptide, the pharmacological effects to saralasin are relatively short-lasting and are only manifest after parenteral administration, oral doses being ineffective. Although the therapeutic uses of peptide AII-blockers, like saralasin, are severely limited due to their oral ineffectiveness and short duration of action, their major utility is as a pharmaceutical standard.

SUMMARY OF THE INVENTION

According to the present invention there is provided a method of treating chronic renal failure mediated by AII in a mammal comprising administering to the mammal a therapeutically effective amount of a pharmaceutical composition having the formula (I):

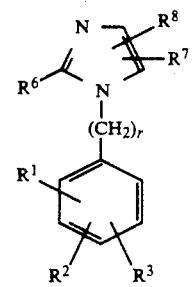

wherein
$R^1$ is 4—$CO_2H$; 4—$CO_2R^9$;

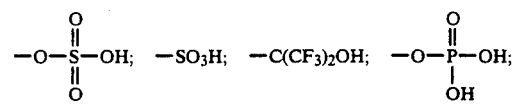

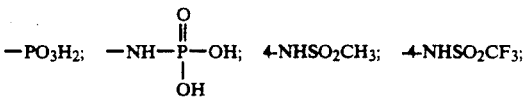

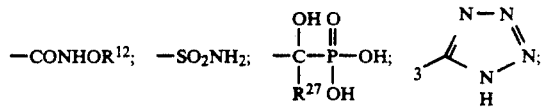

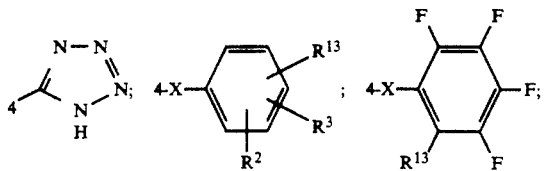

-continued

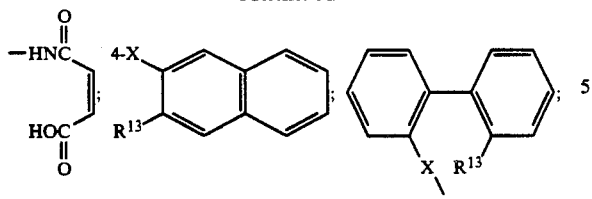

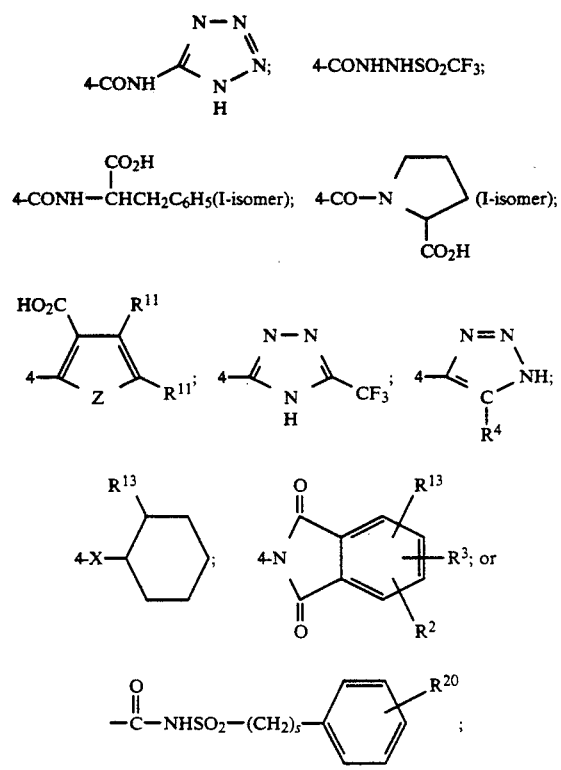

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $NHSO_2CH_3$; $NHSO_2CF_3$; $CONHOR^{12}$; $SO_2NH_2$;

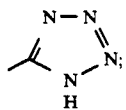

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms, alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl of 4 to 10 carbon atoms; cycloalkylalkenyl or cycloalkylalkynyl of 5 to 10 carbon atoms; $(CH_2)_sZ(CH_2)_mR^5$ optionally substituted with F or $CO_2R^{14}$; benzyl or benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where $v=1-6$; $C_6F_5$; CN;

$$-\overset{O}{\underset{\|}{C}}R^{16};$$

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl; vinyl; alkynyl of 2-10 carbon atoms; phenylalkynyl where the alkynyl portion is 2-6 carbon atoms; heteroaryl selected from 2- and 3-thienyl, 2- and 3-furyl, 2-, 3-, and 4-pyridyl, 2-pyrazinyl, 2-, 4-, and 5-pyrimidinyl, 3- and 4-pyridazinyl, 2-, 4- and 5-thiazolyl, 2-, 4-, and 5-selenazolyl, 2-, 4-, and 5-oxazolyl; 2- or 3-pyrrolyl, 3-, 4- or 5-pyrazolyl, and 2-, 4- or 5-imidazolyl; o-, m- or p-biphenylyl; o-, m- or p-phenoxyphenyl; substituted phenylalkynyl, heteroaryl, biphenyl or phenoxyphenyl as defined above substituted on ring carbon with 1 or 2 substituents selected from halogen, alkoxy of 1-5 carbon atoms, alkyl of 1-5 carbon atoms, $-NO_2$, $-CN$, $-CF_3$, $-COR^{16}$, $-CH_2OR^{17}$, $-NHCOR^{17}$, $CONR^{18}R^{19}$, $S(O)_rR^{17}$, and $SO_2NR^{18}R^{19}$; pyrrolyl, pyrazolyl or imidazolyl as defined above substituted on ring nitrogen with alkyl of 1-5 carbon atoms or benzyl; or substituted alkyl, alkenyl, or alkynyl of 1 to 10 carbon atoms substituted with a substituted or unsubstituted heteroaryl, biphenylyl or phenoxyphenyl group as defined above; any of the foregoing polycyclic aryl groups substituted with 1 or 2 substituents selected from halogen, alkoxy of 1-5 carbon atoms, alkyl of 1-5 carbon atoms, $-NO_2$, $-CN$, $-CF_3$, $-COR^{16}$, $-CH_2OR^{17}$, $-NHCOR^{17}$, $CONR^{18}R^{19}$, $S(O)_rR^{17}$, and $SO_2NR^{18}R^{19}$; the anhydride of 4,5-dicarboxyl-1- or 2-naphthyl; or substituted alkyl of 1 to 10 carbon atoms, alkenyl or alkynyl of 2 to 10 carbon atoms substituted with a substituted or unsubstituted polycyclic aryl group as defined above;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; $-(CH_2)_m$-imidazol-1-yl; $-(CH_2)_m$-1,2,3-triazolyl optionally substituted with one or two groups selected from $CO_2CH_3$ or alkyl of 1 to 4 carbon atoms; $-(CH_2)_s$-tetrazolyl;

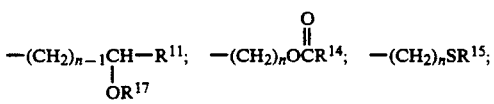

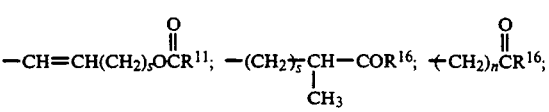

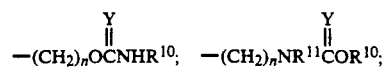

—(CH$_2$)$_n$NR$^{11}$CNHR$^{10}$;  —(CH$_2$)$_n$NR$^{11}$SO$_2$R$^{10}$;

—(CH$_2$)$_n$NR$^{11}$CR$^{10}$;  —(CH$_2$)$_m$F;  —(CH$_2$)$_m$ONO$_2$;  —CH$_2$N$_3$;

—(CH$_2$)$_m$NO$_2$;  —CH=N—NR$^{11}$R$^{17}$;

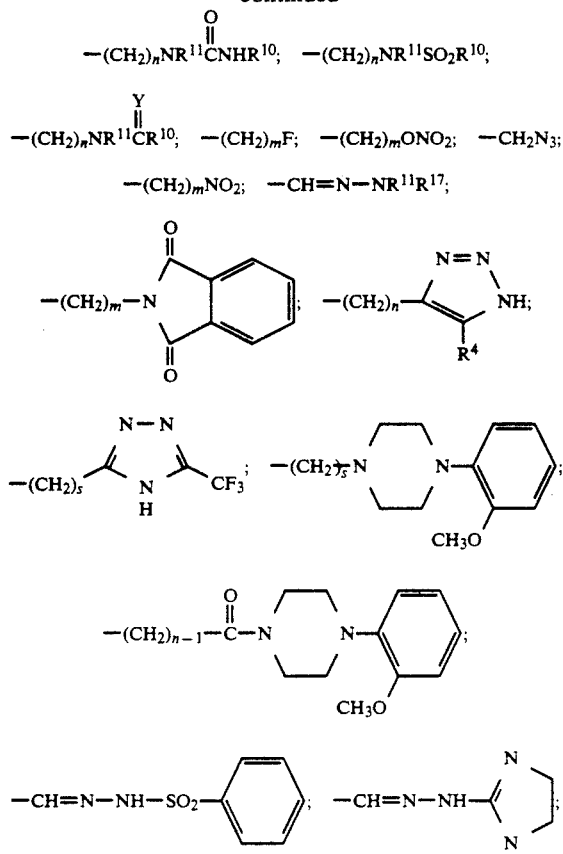

R$^9$ is

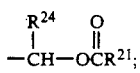

R$^{10}$ is alkyl of 1 to 6 carbon atoms or perfluoroalkyl of 1 to 6 carbon atoms, 1-adamantyl, 1-naphthyl, 1-(1-naphthyl)ethyl, or (CH$_2$)$_p$C$_6$H$_5$;

R$^{11}$ is H, alkyl of 1 to 6 carbon atoms, cycloalkyl of 3 to 6 carbon atoms, phenyl or benzyl;

R$^{12}$ is H, methyl or benzyl;

R$^{13}$ is —CO$_2$H;  —CO$_2$R$^9$;  —CH$_2$CO$_2$H, —CH$_2$CO$_2$R$^9$;

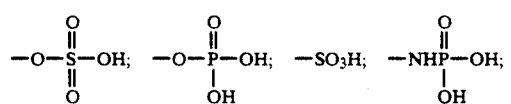

—PO$_3$H$_2$;  —C(CF$_3$)$_2$OH;  —NHSO$_2$CH$_3$;  —NHSO$_2$CF$_3$;

—NHCOCF$_3$;  —CONHOR$^{12}$;  —SO$_2$NH$_2$;

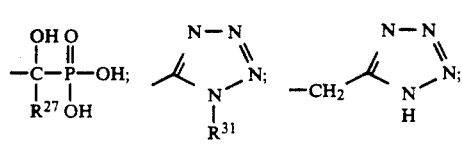

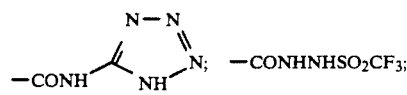

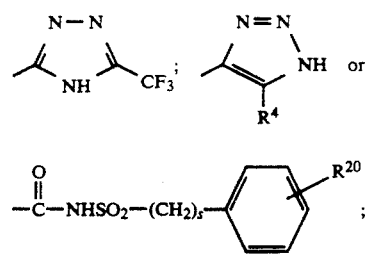

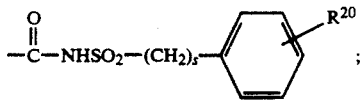

R$^{14}$ is H, alkyl or perfluoroalkyl of 1 to 8 carbon atoms, cycloalkyl of 3 to 6 carbon atoms, phenyl or benzyl;

R$^{15}$ is H, alkyl of 1 to 6 carbon atoms, cycloalkyl of 3 to 6 carbon atoms, phenyl, benzyl, acyl of 1 to 4 carbon atoms, phenacyl;

R$^{16}$ is H, alkyl of 1 to 6 carbon atoms, cycloalkyl of 3 to 6 carbon atoms, (CH$_2$)$_p$C$_6$H$_5$, OR$^{17}$, or NR$^{18}$R$^{19}$;

R$^{17}$ is H, alkyl of 1 to 6 carbon atoms, cycloalkyl of 3 to 6 carbon atoms, phenyl or benzyl;

R$^{18}$ and R$^{19}$ independently are H, alkyl of 1 to 4 carbon atoms, phenyl, benzyl, α-methylbenzyl, or taken together with the nitrogen form a ring of the formula

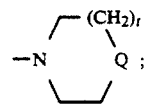

Q is NR$^{20}$, O or CH$_2$;

R$^{20}$ is H, alkyl of 1–4 carbon atoms, or phenyl;

R$^{21}$ is alkyl of 1 to 6 carbon atoms, —NR$^{22}$R$^{23}$, or

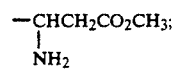

R$^{22}$ and R$^{23}$ independently are H, alkyl of 1 to 6 carbon atoms, benzyl, or are taken together as (CH$_2$)$_u$ where u is 3–6;

R$^{24}$ is H, CH$_3$ or —C$_6$H$_5$;

R$^{25}$ is NR$^{27}$R$^{28}$, OR$^{28}$, NHCONH$_2$, NHCSNH$_2$,

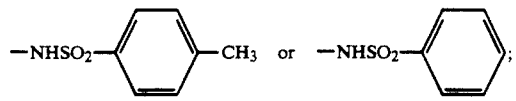

R$^{26}$ is hydrogen, alkyl with from 1 to 6 carbon atoms, benzyl, or allyl;

R$^{27}$ and R$^{28}$ are independently hydrogen, alkyl with from 1 to 5 carbon atoms, or phenyl;

R$^{29}$ and R$^{30}$ are independently alkyl of 1–4 carbon atoms or taken together are —(CH$_2$)$_q$—;

R$^{31}$ is H, alkyl of 1 to 4 carbon atoms, —CH$_2$CH=CH$_2$ or —CH$_2$C$_6$H$_4$R$^{32}$;

R$^{32}$ is H, NO$_2$, NH$_2$, OH or OCH$_3$;

X is a carbon-carbon single bond, —CO—, —CH$_2$—, —O—, —S—, —NH—,

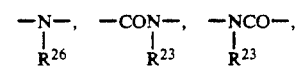

—OCH₂—, —CH₂O—, —SCH₂—, —CH₂S—, —NHC(R²⁷)(R²⁸)—, —NR²³SO₂—, —SO₂NR²³—, —C(R²⁷)(R²⁸)NH—, —CH=CH—, —CF=CF—, —CH=CF—, —CF=CH—, —CH₂CH₂—, —CF₂CF₂—,

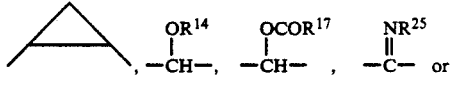

Y is O or S;
Z is O, NR¹¹, or S;
m is 1 to 5;
n is 1 to 10;
p is 0 to 3;
q is 2 to 3;
r is 0 to 2;
s is 0 to 5;
t is 0 or 1;
or a pharmaceutically acceptable salt thereof; provided that:

(1) the R¹ group is not in the ortho position;
(2) when R¹ is

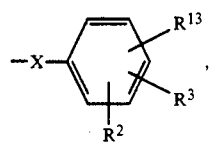

X is a single bond, and R¹³ is CO₂H, or

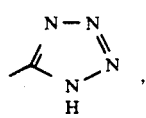

then R¹³ must be in the ortho or meta position; or when R¹ and X are as above and R¹³ is NHSO₂CF₃ or NHSO₂CH₃, R¹³ must be ortho;

(3) when R¹ is

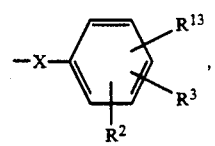

and X is other than a single bond, then R¹³ must be ortho except when X=NR²³CO and R¹³ is NHSO₂CF₃ or NHSO₂CH₃, then R¹³ must be ortho or meta;

(4) when R¹ is 4—CO₂H or a salt thereof, R⁶ cannot be S-alkyl;

(5) when R¹ is 4—CO₂H or a salt thereof, the substituent on the 4-position of the imidazole cannot be CH₂OH, CH₂OCOCH₃, or CH₂CO₂H;

(6) when R¹ is

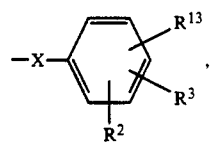

X is —OCH₂—, and R¹³ is 2—CO₂H, and R⁷ is H then R⁶ is not C₂H₅S;

(7) when R¹ is

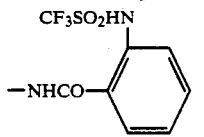

and R⁶ is n-hexyl, then R⁷ and R⁸ are not both hydrogen;

(8) when R¹ is

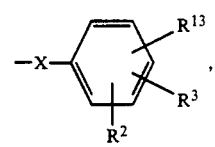

R⁶ is not methoxybenzyl;

(9) the R⁶ group is not —CHFCH₂CH₂CH₃ or CH₂OH;

(10) when r=0, R¹ is

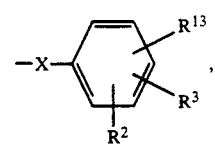

X is —NH—CO—, R¹³ is 2—NHSO₂CF₃, and R⁶ is n-propyl, then R⁷ and R⁸ are not —CO₂CH₃;

(11) when r=0, R¹ is

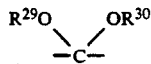

X is —NH—CO—, R¹³ is 2—COOH, and R⁶ is n-propyl, then R⁷ and R⁸ are not —CO₂CH₃;

(12) when r=1, R¹=

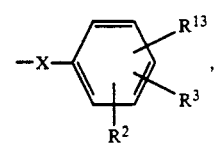

X is a single bond, R⁷ is Cl, and R⁸ is —CHO, then R¹³ is not 3-(tetrazol-5-yl);

(13) when r=1, R¹=

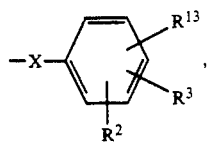

X is a single bond, $R^7$ is Cl, and $R^8$ is —CHO, then $R^{13}$ is not 4-(tetrazol-5-yl).

Preferred in the method of this invention are compounds having the formula (II):

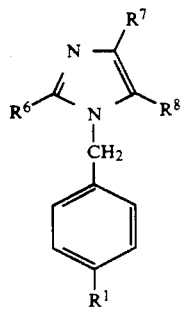

(II)

wherein
$R^1$ is —CO$_2$H; —NHSO$_2$CF$_3$;

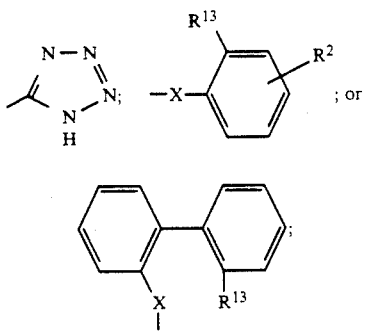
; or $R^6$ is alkyl of 3 to 10 carbon atoms, alkenyl of 3 to 10 carbon atoms, alkynyl of 3 to 10 carbon atoms, cycloalkyl of 3 to 8 carbon atoms, benzyl substituted on the phenyl ring with up to two groups selected from alkoxy of 1 to 4 carbon atoms, halogen, alkyl of 1 to 4 carbon atoms, and nitro;

$R^8$ is

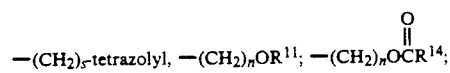

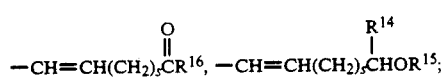

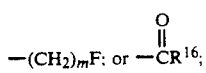

phenylalkenyl wherein the aliphatic portion is 2 to 4 carbon atoms; —(CH$_2$)$_m$-imidazol-1-yl; or —(CH$_2$)$_m$-1,2,3-triazolyl optionally substituted with one two groups selected from —CO$_2$CH$_3$ or alkyl or 1 to 4 carbon atoms;

$R^{13}$ is —CO$_2$H, —CO$_2$R$^9$, NHSO$_2$CF$_3$; SO$_3$H; or

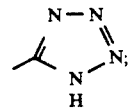

$R^{16}$ is H, alkyl or 1 to 5 carbon atoms, OR$^{17}$, or NR$^{18}$R$^{19}$;

X is carbon-carbon single bond, —CO—, —CH$_2$CH$_2$—,

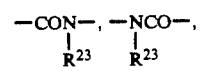

—OCH$_2$—, —CH$_2$O—, —O—, —SCH$_2$—, —CH$_2$S—, —NH—CH$_2$—, —CH$_2$NH— or —CH=CH—; and pharmaceutically acceptable salts of these compounds.

More preferred in the process of the invention are compounds of the preferred scope where:

$R^2$ is H, alkyl of 1 to 4 carbon atoms, halogen, or alkoxy or 1 to 4 carbon atoms;

$R^6$ is alkyl, alkenyl or alkynyl of 3 to 7 carbon atoms;

$R^7$ is heteroaryl selected from 2- and 3-thienyl, 2- and 3-furyl, 2-, 3-, and 4-pyridyl, p-biphenylyl; H, Cl, Br, I; C$_v$F$_{2v+1}$, where v=1-3;

straight or branched chain alkyl of 1 to 6 carbon atoms; or phenyl;

$R^8$ is

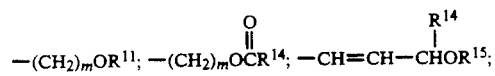

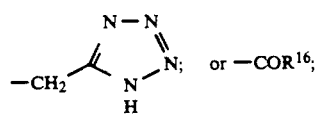

$R^{10}$ is CF$_3$, alkyl or 1 to 6 carbon atoms or phenyl;
$R^{11}$ is H, or alkyl or 1 to 4 carbon atoms;
$R^{13}$ is CO$_2$H; CO$_2$CH$_2$OCOC(CH$_3$)$_3$; NHSO$_2$CF$_3$;

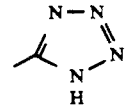

$R^{14}$ is H, or alkyl of 1 to 4 carbon atoms;
$R^{15}$ is H, alkyl or 1 to 4 carbon atoms, or acyl or 1 to 4 carbon atoms;
$R^{16}$ is H, alkyl or 1 to 5 carbon atoms; OR$^{17}$; or

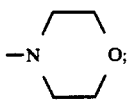

m is 1 to 5;
X=single bond, —O—; —CO—; —NHCO—; or —OCH$_2$—; and
pharmaceutically acceptable salts.

More preferred in the method of the invention are compounds of Formula II, wherein $R^1$ is

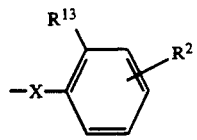

and X is a single bond; and pharmaceutically suitable salts thereof.

Most preferred in the method of the invention are compounds of formula II selected from the following, and pharmaceutically acceptable salts thereof:
2-Butyl-4-chloro-1-[(2'-(1H-tetrazol-5-yl)biphenyl-4-yl)methyl]-5-(hydroxymethyl)imidazole
2-Butyl-4-chloro-1-[(2'-carboxybiphenyl-4-yl)methyl]-5-(hydroxymethyl)imidazole
2-Butyl-4-chloro-1-[(2'-carboxybiphenyl-4-yl)methyl]-5-[(methoxycarbonyl)aminomethyl] imidazole
2-Butyl-4-chloro-1-[(2'-carboxybiphenyl-4-yl)methyl]-5-[(propoxycarbonyl)aminomethyl] imidazole
2-Butyl-4-chloro-1-[(2'-carboxybiphenyl-4-yl)methyl]imidazole-5-carboxaldehyde
2-Butyl-1-[(2'-carboxybiphenyl-4-yl)methyl]imidazole-5-carboxaldehyde
2-(1E-Butenyl)-4-chloro-1-[(2'-carboxybiphenyl-4-yl)methyl]-5-(hydroxymethyl)imidazole
2-(1E-Butenyl)-4-chloro-1-[(2'-carboxybiphenyl-4-yl)methyl]imidazole-5-carboxaldehyde
2-Propyl-4-chloro-1-[(2'-(1H-tetrazol-5-yl)biphenyl-4-yl)methyl]-5-(hydroxymethyl)imidazole
2-Propyl-4-chloro-1-[(2'-(1H-tetrazol-5-yl)biphenyl-4-yl)methyl]imidazole-5-carboxaldehyde
2-Butyl-4-chloro-1-[2'-(1H-tetrazol-5-yl)biphenyl-4-yl)methyl]imidazole-5-carboxaldehyde
2-(1E-Butenyl)-4-chloro-1-[(2'-(1H-tetrazol-5-yl)biphenyl-4-yl)methyl]-5-hydroxymethyl)imidazole
2-(1E-Butenyl)-4-chloro-1-[(2'-(1H-tetrazol-5-yl)biphenyl-4-yl)methyl]imidazole-5-carboxaldehyde
2-Butyl-4-chloro-1-[(2'-(1H-tetrazol-5-yl)-biphenyl-4-yl)methyl]imidazole-5-carboxylic acid
2-Propyl-4-chloro-1-[(2'-(1H-tetrazol-5-yl)biphenyl-4-yl)methyl]imidazole-5-carboxylic acid
2-Propyl-4-trifluoromethyl-1-[(2'-(1H-tetrazol-5-yl)biphenyl-4-yl)methyl]imidazole-5-carboxylic acid
2-Propyl-4-trifluoromethyl-1-[(2'-(1H-tetrazol-5-yl)biphenyl-4-yl)methyl]-5-(hydroxylmethyl)imidazole
2-Butyl-4-trifluoromethyl-1-[(2'-(1H-tetrazol-5-yl)biphenyl-4-yl)methyl]imidazole-5-carboyxlic acid
2-Propyl-4-trifluoromethyl-1-[(2'-(carboxybiphenyl-4-yl)methyl]imidazole-5-carboxaldehyde
2-Propyl-4-pentafluoroethyl-1-[(2'-(1H-tetrazol-5-yl)biphenyl-4-yl)methyl]-5-(hydroxymethyl)-imidazole
2-Propyl-1-[(2'-(1H-tetrazol-5-yl)biphenyl-4-yl)methyl]imidazole-4,5-dicarboxylic acid
2-Propyl-4-pentafluoroethyl-1-[(2'-(1H-tetrazol-5-yl)biphenyl-4-yl)methyl]imidazole-5-carboxylic acid
2-Propyl-4-pentafluoroethyl-[(2'-(1H-tetrazol-5-yl)biphenyl-4-yl)methyl]imidazole-5-carboxaldehyde
1-[(2'-(1H-Tetrazol-5-yl)biphenyl-4-yl)methyl]-4-phenyl-2-propylimidazole-5-carboxaldehyde
1-[(2'-Carboxybiphenyl-4-yl)methyl]-4-phenyl-2-propylimidazole-5-carboxaldehyde Note that throughout the text when an alkyl substituent is mentioned, the normal alkyl structure is meant (i.e., butyl is n-butyl) unless otherwise specified.

Pharmaceutically suitable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

Also within the scope of this invention are methods of using pharmaceutical compositions comprising a suitable pharmaceutical carrier and a compound of Formula (I), to treat chronic renal failure. The pharmaceutical compositions can optionally contain one or more other therapeutic agents. It should be noted in the foregoing structural formula, when a radical can be a substituent in more than one previously defined radical, that first radical can be selected independently in each previously defined radical. For example, $R^1$, $R^2$ and $R^3$ can each be CONHOR$^{12}$. $R^{12}$ need not be the same substituent in each of $R^1$, $R^2$ and $R^3$ but can be selected independently for each of them.

DETAILED DESCRIPTION OF THE INVENTION

The compounds of Formula (I) useful in this invention are described in and prepared by methods set forth in European Patent Application EPA 0 324 377, published Jul. 19, 1989, (page 17, line 5 through page 212, line 32), European Patent Application EPA 0 253,310, published Jan. 20, 1988 (page 15, line 26, through page 276) and copending commonly-assigned U.S. patent application U.S. Ser. No. 07/373,755, filed Jun. 30, 1989, (page 16, line 21 through page 153, line 15), the disclosures of which are hereby incorporated by reference.

It is believed that the compounds described herein are efficacious in the treatment of most chronic renal failure cases mediated by AII. While it is not clear, there is a possibility that the efficacy of these compounds may be limited in the treatment of renal artery stenosis due to a reversible loss of filtration in the stenotic kidney.

The following illustrate the use of nonpeptide AII receptor antagonists to treat chronic renal failure mediated by angiotensin-II:

PARTIALLY NEPHRECTOMIZED RATS

Rats are subjected to five-sixths renal ablation by surgically removing the right kidney and infarction of about two-thirds of the left kidney by ligation of two or three branches of the left renal artery as described by Anderson et al. in J. Clin. Invest., Vol. 76, pages 612–619 (August 1985). Rats are fed standard rat chow containing about 24% protein by weight and are separated into two groups. The rats in Group I are not treated. The rats in Group II are treated over a period of four weeks using one of the compounds described above. Renal hemodynamics and glomerular injury are monitored in both groups of rats after four weeks.

It is expected that the rats in Group I (no treatment) would have high blood pressure, protein urea and glomerular structural lesions whereas the rats in Group II (treatment with the test compound) would have normal blood pressure, less protein urea and fewer glomerular lesions.

STREPTOZOTOCIN-INDUCED DIABETIC RATS

This procedure is described by Zatz et al. in Proc. Natl. Acad. Sci. USA 82: 5963–5967 (September 1985). Rats are studied two to ten weeks after being injected once with streptozotocin (60 mg/kg i.v.). In addition, ultralente insulin is given to maintain the blood glucose level between 200–400 mg/dl. Rats are maintained on diet containing about 50% protein by weight. The rats are then separated into two groups. The rats in Group I are not treated. The Group II rats are treated for about four to five weeks after streptozotocin injection using one of the compounds described above. Renal hemodynamics and glomerular injury are monitored in both groups of rats.

It is expected that the rats in Group I (no treatment) would have normal blood pressure, protein urea, and glomerular structural lesions whereas the rats in Group II (treatment with the test compound) would have slightly lower blood pressure, less protein urea and fewer glomerular lesions.

DOSAGE FORMS

The compounds of this invention can be administered for the treatment of AII-mediated chronic renal failure according to the invention by any means that effects contact of the active ingredient compound with the site of action. For example, administration can be parenteral, i.e., subcutaneous, intravenous, intramuscular, or intraperitoneal. Alternatively, or concurrently, in some cases administration can be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, A. Osol, a standard reference text in this field.

Useful pharmaceutical dosage-forms for administration of the compounds of this invention can be illustrated as follows:

Capsules:

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules:

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets:

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable:

A parenteral composition suitable for administration by injection is prepared by stirring 1.5% by weight of active ingredient in 10% by volume propylene glycol. The solution is made to volume with water for injection and sterilized.

Suspension:

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs.

What is claimed is:

1. A method of treating chronic renal failure mediated by AII in a mammal comprising administering to the mammal a therapeutically effective amount of a pharmaceutical composition having the formula (I):

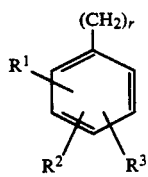

wherein
$R^1$ is 4—$CO_2H$; 4—$CO_2R^9$;

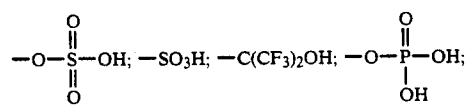

4-$NHSO_2CH_3$; 4-$NHSO_2CF_3$; —$CONHOR^{12}$;

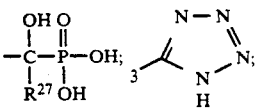

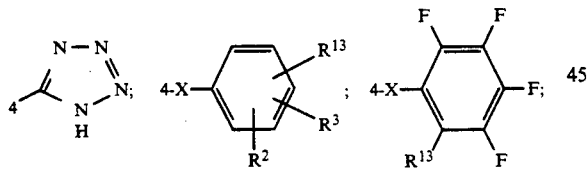

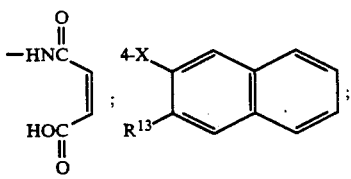

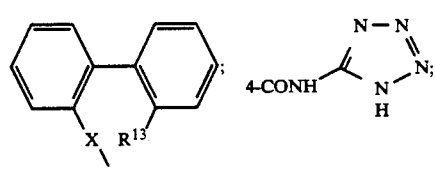

4-$CONHNHSO_2CF_3$; 4-$CONH$—$CHCH_2C_6H_5$(I-isomer);

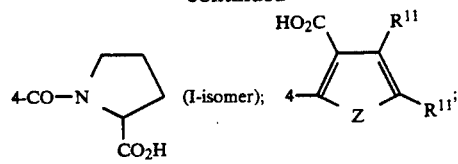

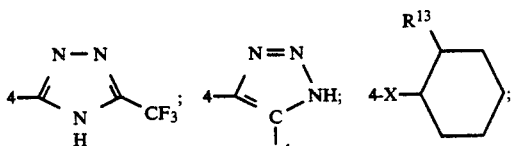

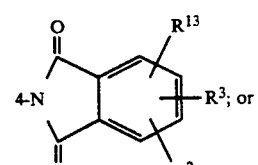

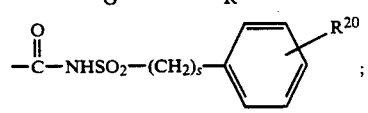

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $NHSO_2CH_3$; $NHSO_2CF_3$; $CONHOR^{12}$; $SO_2NH_2$;

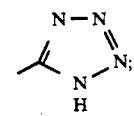

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms, alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl of 4 to 10 carbon atoms; cycloalkylalkenyl or cycloalkylalkynyl of 5 to 10 carbon atoms; $(CH_2)_sZ(CH_2)_mR^5$ optionally substituted with F or $CO_2R^{14}$; benzyl or benzyl substituted on the phenyl ring with 2 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1–6; $C_6F_5$; CN;

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, CF₃, and COOR, and R is H, alkyl of 1 to 4 carbon atoms, or phenyl;

R⁸ is H, CN, alkyl of 1 to 10 carbon atoms, alkenyl of 3 to 10 carbon atoms, or the same groups substituted with F; phenylalkenyl wherein the alkenyl portion is 2 to 6 carbon atoms; —(CH₂)ₘ-imidazol-1-yl; —(CH₂)ₘ-1,2,3-triazolyl optionally substituted with one or two groups selected from CO₂CH₃ or alkyl of 1 to 4 carbon atoms; —(CH₂)ₛ-tetrazolyl;

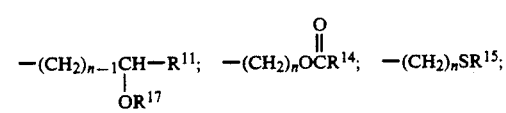

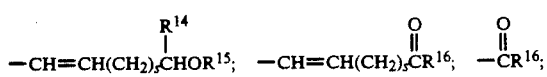

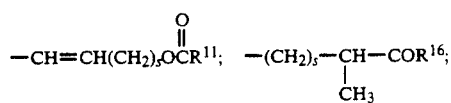

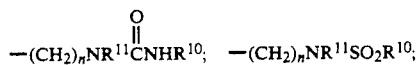

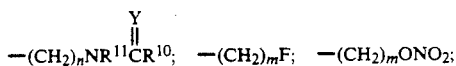

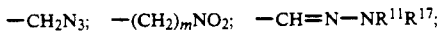

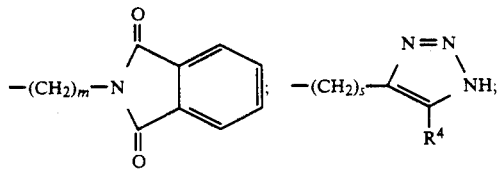

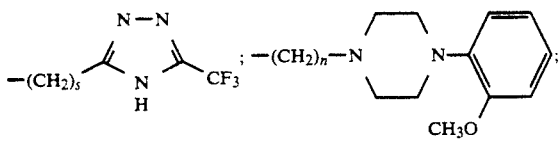

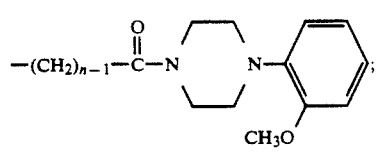

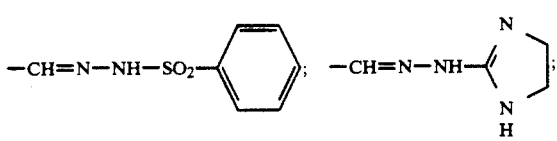

R⁹ is

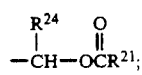

R¹⁰ is alkyl of 1 to 6 carbon atoms or perfluoroalkyl of 1 to 6 carbon atoms, 1-adamantyl, 1-naphthyl, 1-(1-naphthyl)ethyl, or (CH₂)ₚC₆H₅;

R¹¹ is H, alkyl of 1 to 6 carbon atoms, cycloalkyl of 3 to 6 carbon atoms, phenyl or benzyl;

R¹² is H, methyl or benzyl;

R¹³ is —CO₂H; —CO₂R⁹; —CH₂CO₂H, —CH₂CO₂R⁹;

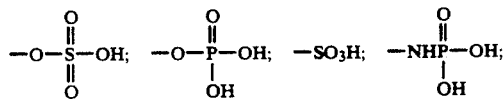

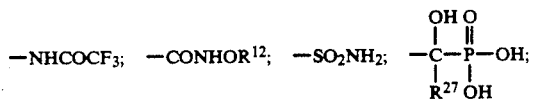

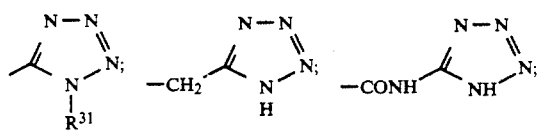

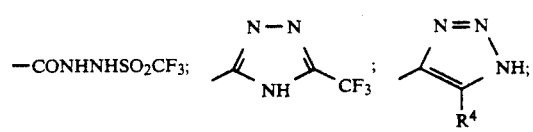

R¹⁴ is H, alkyl or perfluoroalkyl of 1 to 8 carbon atoms, cycloalkyl of 3 to 6 carbon atoms, phenyl or benzyl;

R¹⁵ is H, alkyl of 1 to 6 carbon atoms, cycloalkyl of 3 to 6 carbon atoms, phenyl, benzyl, acyl of 1 to 4 carbon atoms, phenacyl;

R¹⁶ is H, alkyl of 1 to 6 carbon atoms, cycloalkyl of 3 to 6 carbon atoms, (CH₂)ₚC₆H₅, OR¹⁷, or NR¹⁸R¹⁹;

R¹⁷ is H, alkyl of 1 to 6 carbon atoms, cycloalkyl of 3 to 6 carbon atoms, phenyl or benzyl;

R¹⁸ and R¹⁹ independently are H, alkyl of 1 to 4 carbon atoms, phenyl, benzyl, α-methylbenzyl, or taken together with the nitrogen form a ring of the formula

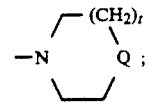

Q is NR²⁰, O or CH₂;

R²⁰ is H, alkyl of 1–4 carbon atoms, or phenyl;

R²¹ is alkyl of 1 to 6 carbon atoms, —NR²²R²³, or

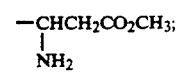

R²² and R²³ independently are H, alkyl of 1 to 6 carbon atoms, benzyl, or are taken together as (CH₂)ᵤ where u is 3–6;

R²⁴ is H, CH₃ or —C₆H₅;

R²⁵ is NR²⁷R²⁸, OR²⁸, NHCONH₂, NHCSNH₂,

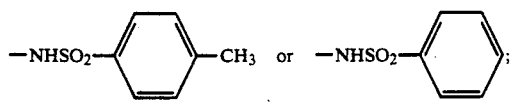

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1-4 carbon atoms or taken together are $-(CH_2)_q-$;

$R^{31}$ is H, alkyl of 1 to 4 carbon atoms, $-CH_2CH=CH_2$ or $-CH_2C_6H_4R^{32}$;

$R^{32}$ is H, $NO_2$, $NH_2$, OH or $OCH_3$;

X is a carbon-carbon single bond, $-CO-$, $-CH_2-$, $-O-$, $-S-$, $-NH-$, $$-\underset{R^{26}}{N}-, \quad -\underset{R^{23}}{CON}-, \quad -\underset{R^{23}}{NCO}-,$$

$-OCH_2-$, $-CH_2O-$, $-SCH_2-$, $-CH_2S-$, $-NHC(R^{27})(R^{28})-$, $-NR^{23}SO_2-$, $-SO_2NR^{23}-$, $-C(R^{27})(R^{28})NH-$, $-CH=CH-$, $-CF=CF-$, $-CH=CF-$, $-CF=CH-$, $-CH_2CH_2-$, $-CF_2CF_2-$,

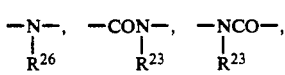

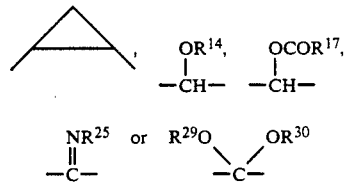

Y is O or S;
Z is O, $NR^{11}$, or S;
m is 1 to 5;
n is 1 to 10;
p is 0 to 3;
q is 2 to 3;
r is 0 to 2;
s is 0 to 5;
t is 0 or 1;
and pharmaceutically acceptable salt of these compounds; provided that:

(1) the $R^1$ group is not in the ortho position;
(2) when $R^1$ is

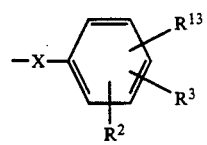

X is a single bond, and $R^{13}$ is $CO_2H$, or

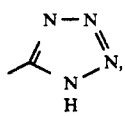

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

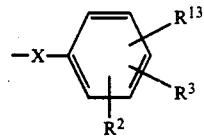

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is $4-CO_2H$ or a salt thereof, $R^6$ cannot be S-alkyl;

(5) when $R^1$ is $4-CO_2H$ or a salt thereof, the substituent on the 4-position of the imidazole cannot be $CH_2OH$, $CH_2OCOCH_3$, or $CH_2CO_2H$;

(6) when $R^1$ is

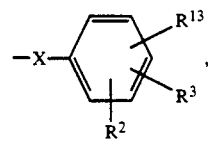

X is $-OCH_2-$, and $R^{13}$ is $2-CO_2H$, and $R^7$ is H then $R^6$ is not $C_2H_5S$;

(7) when $R^1$ is

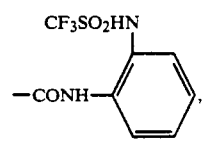

and $R^6$ is n-hexyl, then $R^7$ and $R^8$ are not both hydrogen;

(8) when $R^1$ is

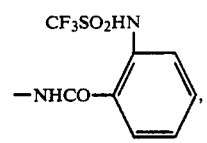

$R^6$ is not methoxybenzyl;

(9) the $R^6$ group is not $-CHFCH_2CH_2CH_3$ or $CH_2OH$;

(10) when r=O, $R^1$ is

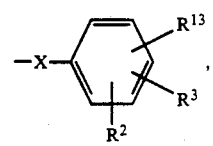

X is $-NH-CO-$, $R^{13}$ is $2-NHSO_2CF_3$, and $R^6$ is n-propyl, then $R^7$ and $R^8$ are not $-CO_2CH_3$;

(11) when r=O, $R^1$ is

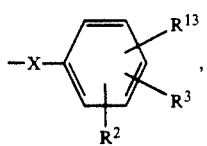

X is —NH—CO—, $R^{13}$ is 2—COOH, and $R^6$ is n-propyl, then $R^7$ and $R^8$ are not —CO$_2$CH$_3$;

(12) when r=1, $R^1$=

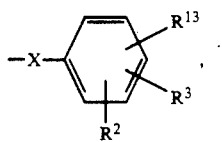

X is a single bond, $R^7$ is Cl, and $R^8$ is —CHO, then $R^{13}$ is not 3-(tetrazol-5-yl);

(13) when r=1, $R^1$=

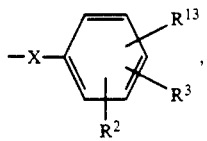

X is a single bond, $R^7$ is Cl, and $R^8$ is —CHO, then $R^{13}$ is not 4-(tetrazol-5-yl).

2. Method of claim 1 wherein, in the compound of formula I is a compound of formula II:

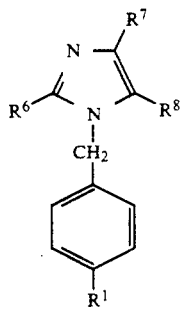

(II)

wherein $R^1$ is —CO$_2$H; —NHSO$_2$CF$_3$;

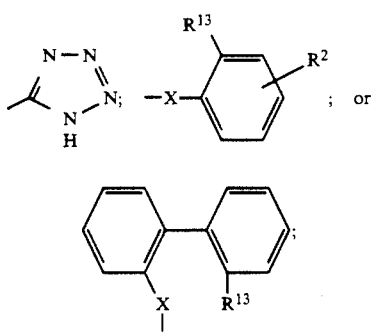

; or $R^6$ is alkyl of 3 to 10 carbon atoms, alkenyl of 3 to 10 carbon atoms, alkynyl of 3 to 10 carbon atoms, cycloalkyl of 3 to 8 carbon atoms, benzyl substituted on the phenyl ring with up to two groups selected from alkoxy of 1 to 4 carbon atoms, halogen, alkyl of 1 to 4 carbon atoms, and nitro;

$R^8$ is

—(CH$_2$)$_s$-tetrazolyl, —(CH$_2$)$_n$OR$^{11}$, —(CH$_2$)$_n$OCR$^{14}$ (C=O);

—CH=CH(CH$_2$)$_s$CR$^{16}$ (C=O), —CH=CH(CH$_2$)$_s$CHOR$^{15}$ (with R$^{14}$);

—(CH$_2$)$_n$CR$^{16}$ (C=O), —(CH$_2$)$_n$NHCOR$^{10}$ (C=O);

—(CH$_2$)$_n$NHSO$_2$R$^{10}$; —(CH$_2$)$_m$F; or —CR$^{16}$ (C=O);

phenylalkenyl wherein the alkenyl portion is 2 to 4 carbon atoms; —(CH$_2$)$_m$-imidazol-1-yl; or —(CH$_2$)$_m$-1,2,3-triazolyl optionally substituted with one or two groups selected from —CO$_2$CH$_3$ or alkyl of 1 to 4 carbon atoms;

$R^{13}$ is —CO$_2$H, —CO$_2$R$^9$, NHSO$_2$CF$_3$; SO$_3$H; or

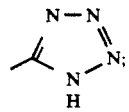

$R^{16}$ is H, alkyl of 1 to 5 carbon atoms, OR$^{17}$, or NR$^{18}$ R$^{19}$; X is carbon-carbon single bond, —CO—, —CH$_2$CH$_2$—,

—CON—, —NCO—,
  |        |
  R$^{23}$    R$^{23}$

—OCH$_2$—, —CH$_2$O—, —O—, —SCH$_2$—, —CH$_2$S—, —NH—CH$_2$—, —CH$_2$NH— or —CH=CH—; or a pharmaceutically acceptable salt thereof.

3. Method of claim 2 wherein the compound of formula II is a compound wherein:
$R^2$ is H, alkyl of 1 to 4 carbon atoms, halogen, or alkoxy of 1 to 4 carbon atoms;
$R^6$ is alkyl, alkenyl or alkynyl of 3 to 7 carbon atoms;
$R^7$ is H, Cl, Br, I; C$_v$F$_{2v+1}$, where v=1-3;

straight or branched chain alkyl of 1 to 6 carbon atoms; or phenyl;
$R^8$ is

—(CH$_2$)$_m$OR$^{11}$; —(CH$_2$)$_m$OCR$^{14}$ (C=O); —CH=CH—CHOR$^{15}$ (with R$^{14}$);

—(CH$_2$)$_m$CR$^{16}$ (C=O); —CH$_2$NHCOR$^{10}$ (C=O); —(CH$_2$)$_m$NHSO$_2$R$^{10}$;

-continued

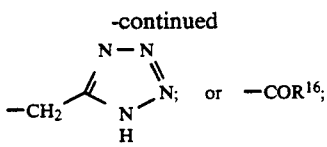

R[10] is CF$_3$, alkyl of 1 to 6 carbon atoms or phenyl;
R[11] is H, or alkyl of 1 to 4 carbon atoms;
R[13] is CO$_2$H; CO$_2$CH$_2$OCOC(CH$_3$)$_3$; NHSO$_2$CF$_3$;

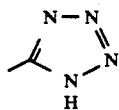

R[14] is H, or alkyl of 1 to 4 carbon atoms;
R[15] is H, alkyl of 1 to 4 carbon atoms, or acyl of 1 to 4 carbon atoms;
R[16] is H, alkyl of 1 to 5 carbon atoms; OR[17]; or

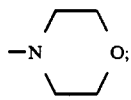

m is 1 to 5;
X=single bond, —O—; —CO—; —NHCO—; or —OCH$_2$—; or
a pharmaceutically acceptable salt thereof.

4. Method of claim 3 wherein the compound of formula II is a compound wherein R[1] is

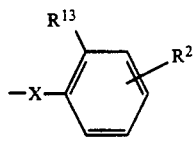

and X is a single bond; or a pharmaceutically suitable salt thereof.

5. Method of claim 4 wherein the compound of formula II is 2-Butyl-4-chloro-1-[(2'-(1H-tetrazol-5-yl)biphenyl-4-yl)methyl]-5-(hydroxymethyl)imidazole or a pharmaceutically acceptable salt thereof.

6. Method of claim 4 wherein the compound of formula II is 2-Butyl-4-chloro-1-[(2'-carboxybiphenyl-4-yl)methyl]-5-(hydroxymethyl)imidazole or a pharmaceutically acceptable salt thereof.

7. Method of claim 4 wherein the compound of formula II is 2-Butyl-4-chloro-1-[(2'-carboxybiphenyl-4-yl)methyl]-5-[(methoxycarbonyl)aminomethyl]imidazole or a pharmaceutically acceptable salt thereof.

8. Method of claim 4 wherein the compound of formula II is 2-Butyl-4-chloro-1-[(2'-carboxybiphenyl-4-yl)methyl]-5-[(propoxycarbonyl)aminomethyl]imidazole or a pharmaceutically acceptable salt thereof.

9. Method of claim 4 wherein the compound of formula II is 2-Butyl-4-chloro-1-[(2'-carboxybiphenyl-4-yl)methyl]imidazole-5-carboxaldehyde or a pharmaceutically acceptable salt thereof.

10. Method of claim 4 wherein the compound of formula II is 2-Butyl-1-[(2'-carboxybiphenyl-4-yl)methyl]-imidazole-5-carboxaldehyde or a pharmaceutically acceptable salt thereof.

11. Method of claim 4 wherein the compound of formula II is 2-(1E-Butenyl)-4-chloro-1-[(2'-carboxybiphenyl-4-yl)methyl]-5-(hydroxymethyl)imidazole or a pharmaceutically acceptable salt thereof.

12. Method of claim 4 wherein the compound of formula II is 2-(1E-Butenyl)-4-chloro-1-[(2'-carboxybiphenyl-4-yl)methyl]imidazole-5-carboxaldehyde or a pharmaceutically acceptable salt thereof.

13. Method of claim 4 wherein the compound of formula II is 2-Propyl-4-chloro-1-[(2'-(1H-tetrazol-5-yl)biphenyl-4-yl)methyl]-5-(hydroxymethyl) imidazole or a pharmaceutically acceptable salt thereof.

14. Method of claim 4 wherein the compound of formula II is 2-Propyl-4-chloro-1-[(2'-(1H-tetrazol-5-yl)biphenyl-4-yl)methyl]imidazole-5-carboxaldehyde or a pharmaceutically acceptable salt thereof.

15. Method of claim 4 wherein the compound of formula II is 2-Butyl-4-chloro-1-[2'-(1H-tetrazol-5-yl)biphenyl-4-yl)methyl]imidazole-5-carboxaldehyde or a pharmaceutically acceptable salt thereof.

16. Method of claim 4 wherein the compound of formula II is 2-(1E-Butenyl)-4-chloro-1-[(2'-(1H-tetrazol-5-yl)biphenyl-4-yl)methyl]-5-hydroxymethyl)imidazole or a pharmaceutically acceptable salt thereof.

17. Method of claim 4 wherein the compound of formula II is 2-(1E-Butenyl)-4-chloro-1-[(2'-(1H-tetrazol-5-yl)biphenyl-4-yl)methyl]imidazole-5-carboxaldehyde or a pharmaceutically acceptable salt thereof.

18. Method of claim 4 wherein the compound of formula II is 2-Butyl-4-chloro-1-[(2'-(1H-tetrazol-5-yl)-biphenyl-4-yl)methyl]imidazole-5-carboxylic acid or a pharmaceutically acceptable salt thereof.

19. Method of claim 4 wherein the compound of formula II is 2-Propyl-4-chloro-1-[(2'-(1H-tetrazol-5-yl)-biphenyl-4-yl)methyl]imidazole-5-carboxylic acid or a pharmaceutically acceptable salt thereof.

20. Method of claim 4 wherein the compound of formula II is 2-Propyl-4-trifluoromethyl-1-[(2'-(1H-tetrazol-5-yl)biphenyl-4-yl)methyl]imidazole-5-carboxylic acid or a pharmaceutically acceptable salt thereof.

21. Method of claim 4 wherein the compound of formula II is 2-Propyl-4-trifluoromethyl-1-[(2'-(1H-tetrazol-5-yl)biphenyl-4-yl)methyl]-5-(hydroxylmethyl)imidazole or a pharmaceutically acceptable salt thereof.

22. Method of claim 4 wherein the compound of formula II is 2-Butyl-4-trifluoromethyl-1-[(2'-(1H-tetrazol-5-yl)biphenyl-4-yl)methyl]imidazole-5-carboxylic acid or a pharmaceutically acceptable salt thereof.

23. Method of claim 4 wherein the compound of formula II is 2-Propyl-4-trifluoromethyl-1-[(2'-(carboxybiphenyl-4-yl)methyl]imidazole-5-carboxaldehyde or a pharmaceutically acceptable salt thereof.

24. Method of claim 4 wherein the compound of formula II is 2-Propyl-4-pentafluoroethyl-1-[(2'-(1H-tetrazol-5-yl)biphenyl-4-yl)methyl]-5-(hydroxymethyl)imidazole or a pharmaceutically acceptable salt thereof.

25. Method of claim 4 wherein the compound of formula II is 2-Propyl-4-pentafluoroethyl-1-[(2'-(1H-tetrazol-5-yl)biphenyl-4-yl)methyl]imidazole-5-carboxylic acid or a pharmaceutically acceptable salt thereof.

26. Method of claim 4 wherein the compound of formula II is 2-Propyl-4-pentafluoroethyl-[(2'-(1H-tetrazol-5-yl)biphenyl-4-yl)methyl]imidazole-5-carboxaldehyde or a pharmaceutically acceptable salt thereof.

27. Method of claim 4 wherein the compound of formula II is 1-[(2'-(1H-Tetrazol-5-yl)biphenyl-4-yl)methyl]-4-phenyl-2-propylimidazole-5-carboxaldehyde or a pharmaceutically acceptable salt thereof.

28. Method of claim 4 wherein the compound of formula II is 1-[(2'-Carboxybiphenyl-4-yl)methyl]-4-phenyl-2-propylimidazole-5-carboxaldehyde or a pharmaceutically acceptable salt thereof.

29. A method of treating chronic renal failure mediated by AII in a mammal comprising administering to the mammal a therapeutically effective amount of a pharmaceutical composition having the formula (I):

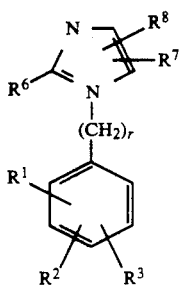

wherein
R$^1$ is 4—CO$_2$H; 4—CO$_2$R$^9$;

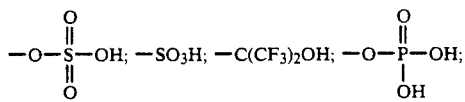

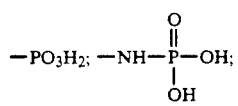

4-NHSO$_2$CH$_3$; —4-NHSO$_2$CF$_3$; —CONHOR$^{12}$;

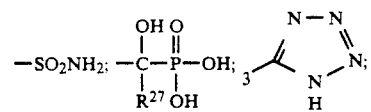

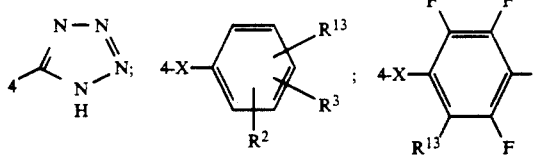

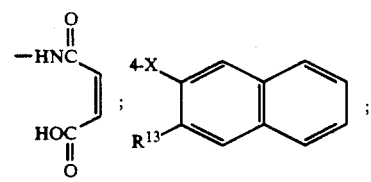

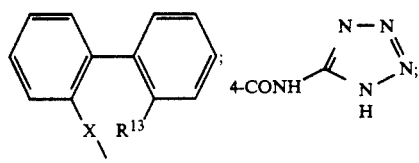

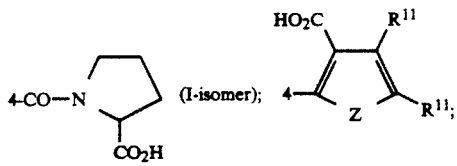

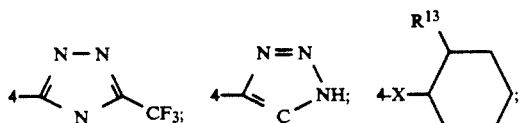

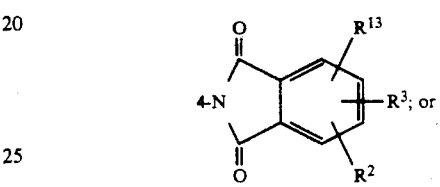

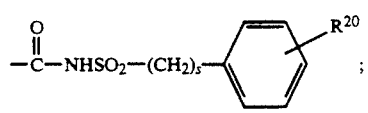

R$^2$ is H; Cl; Br; I; F; NO$_2$; CN; alkyl of 1 to 4 carbon atoms; acyloxy of 1 to 4 carbon atoms; alkoxy of 1 to 4 carbon atoms; CO$_2$H; CO$_2$R$^9$; NHSO$_2$CH$_3$; NHSO$_2$CF$_3$; CONHOR$^{12}$; SO$_2$NH$_2$;

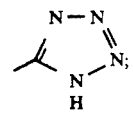

aryl; or furyl;
R$^3$ is H; Cl, Br, I or F; alkyl of 1 to 4 carbon atoms or alkoxy of 1 to 4 carbon atoms;
R$^4$ is CN, NO$_2$ or CO$_2$R$^{11}$;
R$^5$ is H, alkyl of 1 to 6 carbon atoms, cycloalkyl of 3 to 6 carbon atoms, alkenyl or alkynyl of 2 to 4 carbon atoms;
R$^6$ is alkyl of 2 to 10 carbon atoms, alkenyl or alkynyl of 3 to 10 carbon atoms or the same groups substituted with F or CO$_2$R$^{14}$; cycloalkyl of 3 to 8 carbon atoms, cycloalkylalkyl of 4 to 10 carbon atoms; cycloalkylalkenyl or cycloalkylalkynyl of 5 to 10 carbon atoms; (CH$_2$)$_s$Z(CH$_2$)$_m$R$^5$ optionally substituted with F or CO$_2$R$^{14}$; benzyl or benzyl substituted on the phenyl ring with 1 or 2 halogens, alkoxy of 1 to 4 carbon atoms, alkyl of 1 to 4 carbon atoms or nitro;
R$^7$ is H, F, Cl, Br, I, NO$_2$, C$_v$F$_{2v+1}$, where v=1-6; C$_6$F$_5$; CN;

straight or branched alkyl of 1 to 6 carbon atoms; phenyl or phenylalkyl, where alkyl is 1 to 3 carbon atoms; or substituted phenyl or substituted phenyl-alkyl, where alkyl is 1 to 3 carbon atoms, substituted with one or two substituents selected from alkyl of 1 to 4 carbon atoms, F, Cl, Br, OH, OCH$_3$, CF$_3$, and COOR, where R is H, alkyl of 1 to 4 carbon atoms, or phenyl;

R$^8$ is H, CN, alkyl of 1 to 10 carbon atoms, alkenyl of 3 to 10 carbon atoms, or the same groups substituted with F; phenylalkenyl wherein the alkenyl portion is 2 to 6 carbon atoms; —(CH$_2$)$_m$-imidazol-1-yl; —(CH$_2$)$_m$-1,2,3-triazolyl optionally substituted with one or two groups selected from CO$_2$CH$_3$ or alkyl of 1 to 4 carbon atoms; —(CH$_2$)$_s$-tetrazolyl;

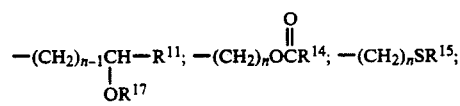

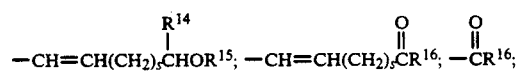

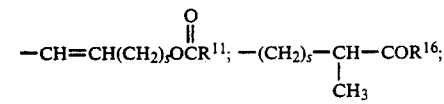

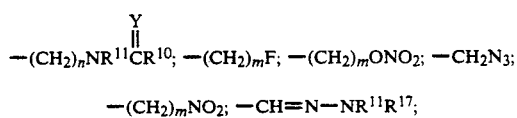

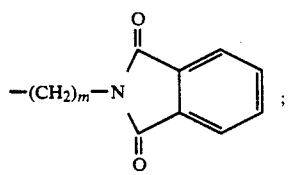

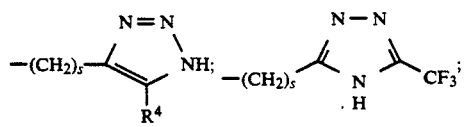

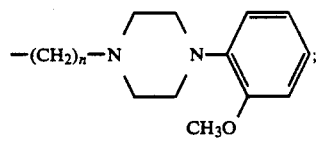

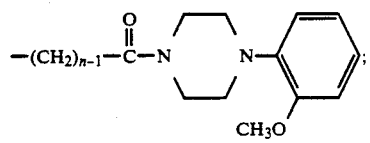

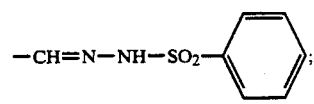

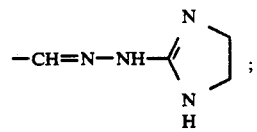

R$^9$ is

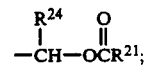

R$^{10}$ is alkyl of 1 to 6 carbon atoms or perfluoroalkyl of 1 to 6 carbon atoms, 1-adamantyl, 1-naphthyl, 1-(1-naphthyl)ethyl, or (CH$_2$)$_p$C$_6$H$_5$;

R$^{11}$ is H, alkyl of 1 to 6 carbon atoms, cycloalkyl of 3 to 6 carbon atoms, phenyl or benzyl;

R$^{12}$ is H, methyl or benzyl;

R$^{13}$ is —CO$_2$H; —CO$_2$R$^9$; —CH$_2$CO$_2$H, —CH$_2$CO$_2$R$^9$;

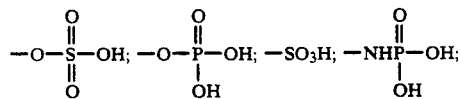

—PO$_3$H$_2$; —C(CF$_3$)$_2$OH; —NHSO$_2$CH$_3$; —NHSO$_2$CF$_3$; —NHCOCF$_3$; —CONHOR$^{12}$; —SO$_2$NH$_2$;

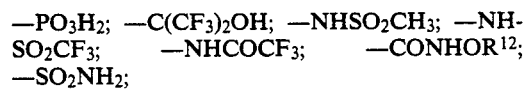

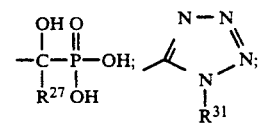

—CONHNHSO$_2$CF$_3$;

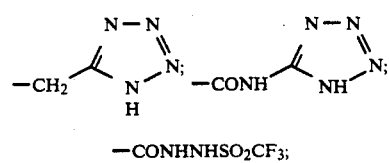

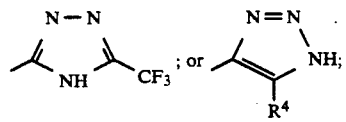

R$^{14}$ is H, alkyl or perfluoroalkyl of 1 to 8 carbon atoms, cycloalkyl of 3 to 6 carbon atoms, phenyl or benzyl;

R$^{15}$ is H, alkyl of 1 to 6 carbon atoms, cycloalkyl of 3 to 6 carbon atoms, phenyl, benzyl, acyl of 1 to 4 carbon atoms, phenacyl;

R$^{16}$ is H, alkyl of 1 to 6 carbon atoms, cycloalkyl of 3 to 6 carbon atoms, (CH$_2$)$_p$C$_6$H$_5$, OR$^{17}$, or NR$^{18}$R$^{19}$;

R$^{17}$ is H, alkyl of 1 to 6 carbon atoms, cycloalkyl of 3 to 6 carbon atoms, phenyl or benzyl;

R$^{18}$ and R$^{19}$ independently are H, alkyl of 1 to 4 carbon atoms, phenyl, benzyl, α-methylbenzyl, or taken together with the nitrogen form a ring of the formula

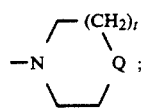

Q is $NR^{20}$, O or $CH_2$;
$R^{20}$ is H, alkyl of 1-4 carbon atoms, or phenyl;
$R^{21}$ is alkyl of 1 to 6 carbon atoms, $-NR^{22}R^{23}$, or

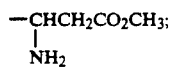

$R^{22}$ and $R^{23}$ independently are H, alkyl of 1 to 6 carbon atoms, benzyl, or are taken together as $(CH_2)_u$ where u is 3-6;
$R^{24}$ is H, $CH_3$ or $-C_6H_5$;
$R^{25}$ is $NR^{27}R^{28}$, $OR^{28}$, $NHCONH_2$, $NHCSNH_2$,

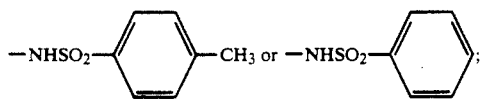

$R^{26}$ is hydrogen, alkyl with from 1 to 6 carbon atoms, benzyl, or allyl;
$R^{27}$ and $R^{28}$ are independently hydrogen, alkyl with from 1 to 5 carbon atoms, or phenyl;
$R^{29}$ and $R^{30}$ are independently alkyl of 1-4 carbon atoms or taken together are $-(CH_2)_q-$;
$R^{31}$ is H, alkyl of 1 to 4 carbon atoms; $-CH_2CH=CH_2$ or $-CH_2C_6H_4R^{32}$;
$R^{32}$ is H, $NO_2$, $NH_2$, OH or $OCH_3$;
X is a carbon-carbon single bond, $-CO-$, $-CH_2-$, $-O-$, $-S-$, $-NH-$,

$-OCH_2-$, $-CH_2O-$, $-SCH_2-$, $-CH_2S-$, $-NHC(R^{27})(R^{28})-$, $-NR^{23}SO_2-$, $-SO_2NR^{23}-$, $-C(R^{27})(R^{28})NH-$, $-CH=CH-$, $-CF=CF-$, $-CH=CF-$, $-CF=CH-$, $-CH_2CH_2-$, $-CF_2CF_2-$,

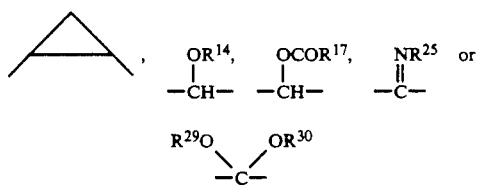

Y is O or S;
Z is O, $NR^{11}$, or S;
m is 1 to 5;
n is 1 to 10;
p is 0 to 3;
q is 2 to 3;
r is 0 to 2;
s is 0 to 5;
t is 0 or 1;

or a pharmaceutically acceptable salt thereof; provided that:
(1) the $R^1$ group is not in the ortho position;
(2) when $R^1$ is

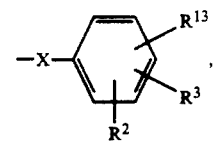

X is a single bond, and $R^{13}$ is $CO_2H$, or

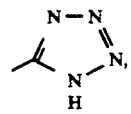

then $R^{13}$ must be in the ortho or meta position; or when $R^1$ and X are as above and $R^{13}$ is $NHSO_2CF_3$ or $NHSO_2CH_3$, $R^{13}$ must be ortho;
(3) when $R^1$ is

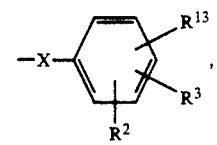

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;
(4) when $R^1$ is $4-CO_2H$ or a salt thereof, $R^6$ cannot be S-alkyl;
(5) when $R^1$ is $4-CO_2H$ or a salt thereof, the substituent on the 4-position of the imidazole cannot be $CH_2OH$, $CH_2OCOCH_3$, or $CH_2CO_2H$;
(6) when $R^1$ is

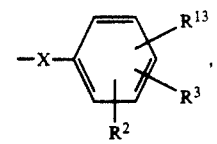

X is $-OCH_2-$, and $R^{13}$ is $2-CO_2H$, and $R^7$ is H then $R^6$ is not $C_2H_5S$;
(7) when $R^1$ is

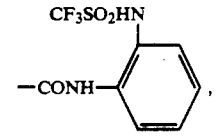

and $R^6$ is n-hexyl, then $R^7$ and $R^8$ are not both hydrogen;
(8) when $R^1$ is

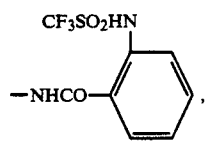

$R^6$ is not methoxybenzyl;

(9) the $R^6$ group is not —CHFCH$_2$CH$_2$CH$_3$ or CH$_2$OH;

(10) when r=0, $R^1$ is

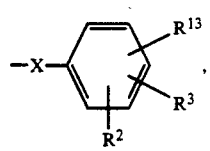

X is —NH—CO—, $R^{13}$ is 2—NHSO$_2$CF$_3$, and $R^6$ is n-propyl, then $R^7$ and $R^8$ are not —CO$_2$CH$_3$;

(11) when r=0, $R^1$ is

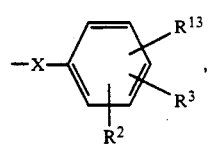

X is NH—CO—, $R^{13}$ is 2—COOH, and $R^6$ is n-propyl, then $R^7$ and $R^8$ are not —CO$_2$CH$_3$;

(12) when r=1, $R^1$=

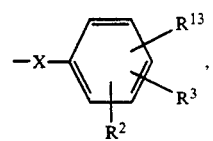

X is a single bond, $R^7$ is Cl, and $R^8$ is —CHO, then $R^{13}$ is not 3-(tetrazol-5-yl);

(13) when r=1, $R^1$=

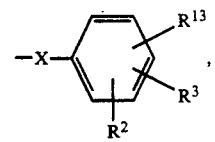

X is a single bond, $R^7$ is Cl, and $R^8$ is —CHO, then $R^{13}$ is not 4-(tetrazol-5-yl).

30. A method of treating chronic renal failure mediated by AII in a mammal comprising administering to the mammal a therapeutically effective amount of a pharmaceutical composition having the formula (I):

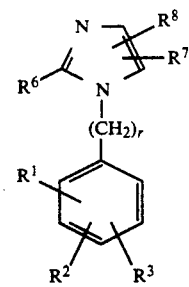

wherein
$R^1$ is 4—CO$_2$H; 4—CO$_2$R$^9$;

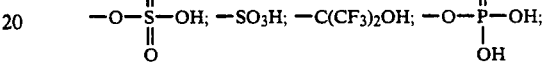

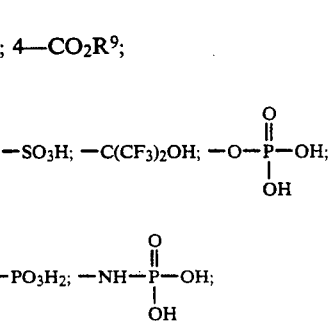

4—NHSO$_2$CH$_3$; —4—NHSO$_2$CF$_3$; —CONHOR$^{12}$;

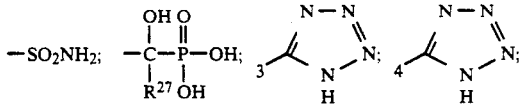

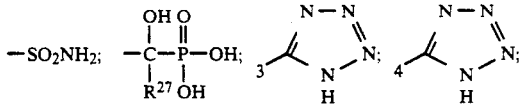

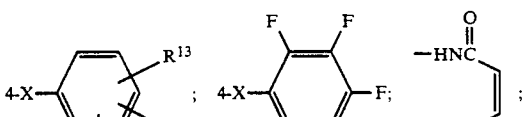

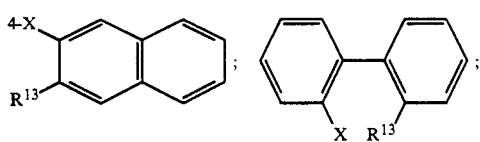

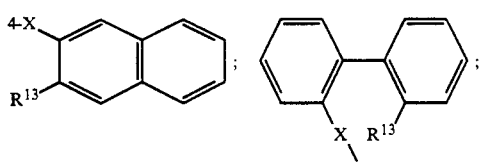

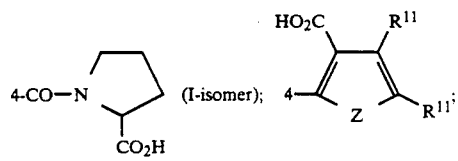

-continued

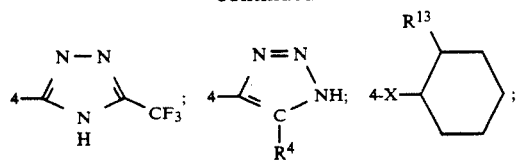 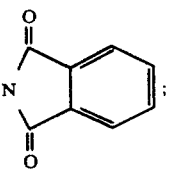

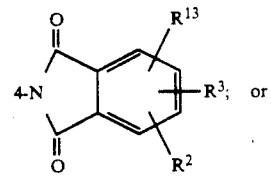

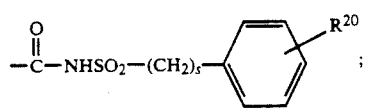

$R^2$ is H; Cl; Br; I; F; $NO_2$; alkyl of 1 to 4 carbon atoms; acyloxy of 1 to 4 carbon atoms; alkoxy of 1 to 4 carbon atoms; $CO_2H$; $CO_2R^9$; $NHSO_2CH_3$; $NHSO_2CF_3$; $CONHOR^{12}$; $SO_2NH_2$; aryl; or furyl; or

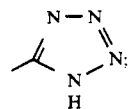

$R^7$ is H, F, Cl, Br, I, $NO_2$, $C_vF_{2v+1}$, where v=1-6; $C_6F_5$; CN;

$R^8$ is H, CN, alkyl of 1 to 10 carbon atoms, alkenyl of 3 to 10 carbon atoms, or the same groups substituted with F; phenylalkenyl wherein the alkenyl portion is 2 to 6 carbon atoms; —$(CH_2)_m$-imidazol-1-yl; —$(CH_2)_m$-1,2,3-triazolyl optionally substituted with one or two groups selected from $CO_2CH_3$ or alkyl of 1 to 4 carbon atoms; —$(CH_2)_m$-tetrazolyl;

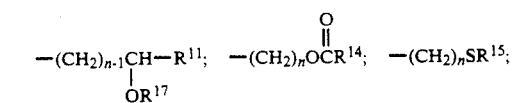

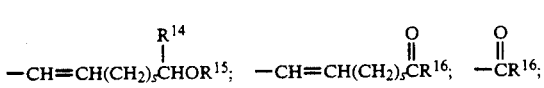

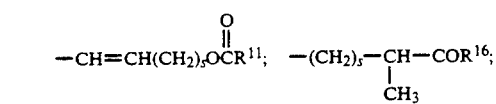

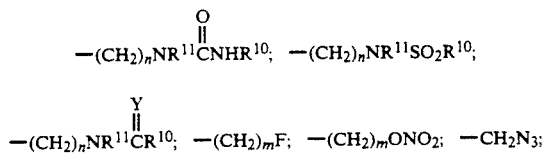

-continued

—$(CH_2)_mNO_2$ or 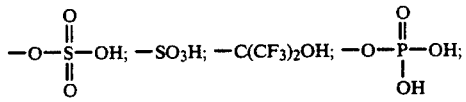

X is a carbon-carbon single bond, —CO—, —O—, —S—, —NH—, —$NR^{26}$—, —$CONR^{23}$—, —$NR^{23}CO$—, —$OCH_2$—, —$CH_2O$—, —$SCH_2$—, —$CH_2S$—, —$NHC(R^{27})(R^{28})$—, —$NR^{23}SO_2$—, —$SO_2NR^{23}$—, $C(R^{27})(R^{28})NH$—, —CH=CH—, —CF=CF—, —CH=CF—, —CF=CH—, —$CH_2CH_2$—, —$CF_2CF_2$—,

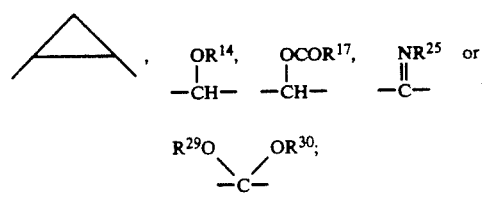

or pharmaceutically suitable salt thereof.

31. A method of treating chronic renal failure mediated by AII in a mammal comprising administering to the mammal a therapeutically effective amount of a pharmaceutical composition having the formula (I):

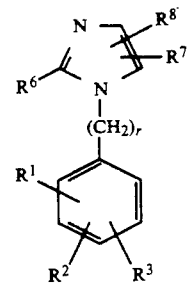

wherein
$R^1$ is 4—$CO_2H$; 4—$CO_2R^9$;

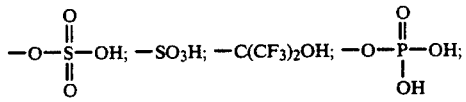

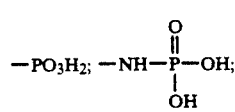

4—$NHSO_2CH_3$; —4—$NHSO_2CF_3$; —CONHOR$^{12}$;

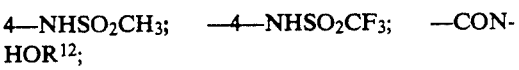

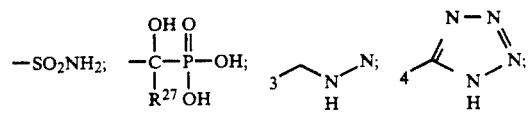

-continued

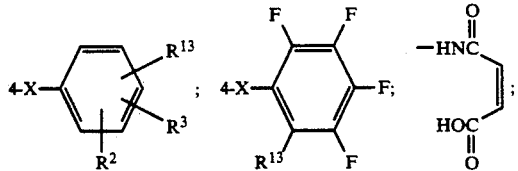

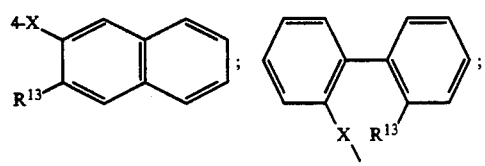

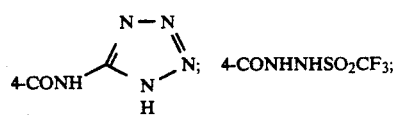

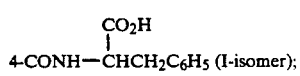

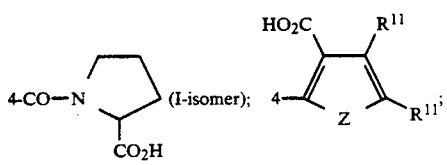

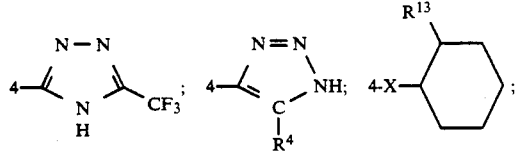

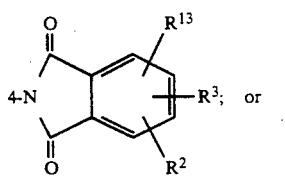

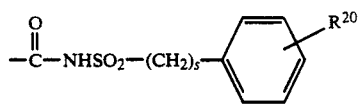

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $NHSO_2CH_3$; $NHSO_2CF_3$; $CONHOR^{12}$; $SO_2NH_2$;

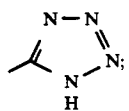

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms, alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl of 4 to 10 carbon atoms; cycloalkylalkenyl or cycloalkylalkynyl of 5 to 10 carbon atoms; $(CH_2)_sZ(CH_2)_mR^5$ optionally substituted with F or $CO_2R^{14}$; benzyl or benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1–6; $C_6F_5$; CN;

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is

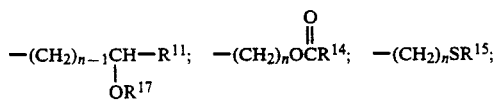

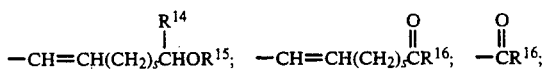

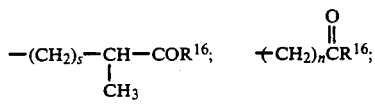

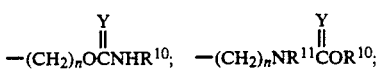

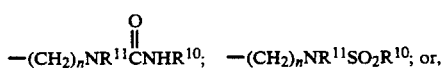

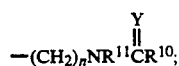

$R^9$ is $$-\overset{R^{24}}{\underset{|}{CH}}-O\overset{O}{\underset{\|}{C}}R^{21};$$

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is —CO$_2$H; —CO$_2$R$^9$; —CH$_2$CO$_2$H, —CH$_2$CO$_2$R$^9$;

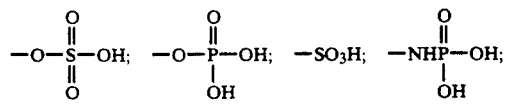

—PO$_3$H$_2$; —C(CF$_3$)$_2$OH; —NHSO$_2$CH$_3$; —NHSO$_2$CF$_3$;

—NHCOCF$_3$; —CONHOR$^{12}$; —SO$_2$NH$_2$;

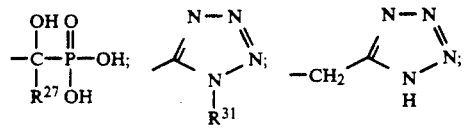

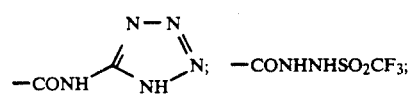

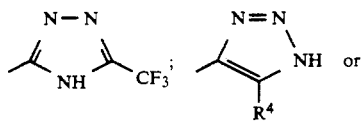

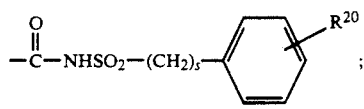

—PO$_3$H$_2$; —C(CF$_3$)$_2$OH; —NHSO$_2$CH$_3$; —NHSO$_2$CF$_3$; —NHCOCF$_3$; —CONHOR$^{12}$; —SO$_2$NH$_2$;

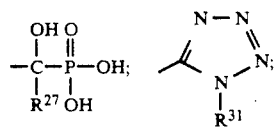

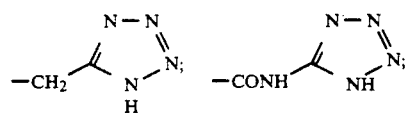

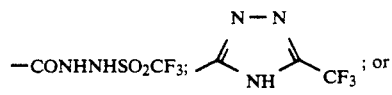

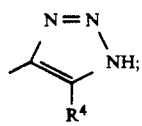

$R^{14}$ is H, alkyl or perfluoroalkyl of 1 to 8 carbon atoms, cycloalkyl of 3 to 6 carbon atoms, phenyl, or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, (CH$_2$)$_p$C$_6$H$_5$, OR$^{17}$, or NR$^{18}$R$^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

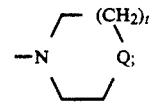

Q is NR$^{20}$, O or CH$_2$;
$R^{20}$ is H, alkyl of 1–4 carbon atoms, or phenyl;
$R^{21}$ is alkyl of 1 to 6 carbon atoms, —NR$^{22}$R$^{23}$, or

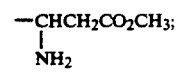

$R^{22}$ and $R^{23}$ independently are H, alkyl of 1 to 6 carbon atoms, benzyl, or are taken together as (CH$_2$)$_u$ where u is 3–6;
$R^{24}$ is H, CH$_3$ or —C$_6$H$_5$;
$R^{25}$ is NR$^{27}$R$^{28}$, OR$^{28}$, NHCONH$_2$, NHCSNH$_2$,

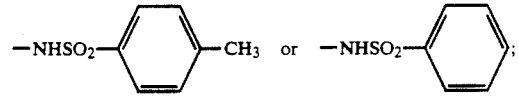

$R^{26}$ is hydrogen, alkyl with from 1 to 6 carbon atoms, benzyl, or allyl;
$R^{27}$ and $R^{28}$ are independently hydrogen, alkyl with from 1 to 5 carbon atoms, or phenyl;
$R^{29}$ and $R^{30}$ are independently alkyl of 1–4 carbon atoms or taken together are —(CH$_2$)$_q$—;
$R^{31}$ is H, alkyl of 1 to 4 carbon atoms, —CH$_2$CH=CH$_2$ or —CH$_2$C$_6$H$_r$R$^{32}$;
$R^{32}$ is H, NO$_2$, NH$_2$, OH or OCH$_3$;
X is a carbon-carbon single bond, —CO—, —CH$_2$—, —O—, —S—, —NH—,

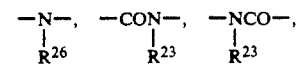

—OCH$_2$—, —CH$_2$O—, —SCH$_2$—, —CH$_2$S—, —NHC(R$^{27}$)(R$^{28}$)—, —NR$^{23}$SO$_2$—, —SO$_2$NR$^{23}$—, —C(R$^{27}$)(R$^{28}$)NH—, —CH=CH—, —CF=CF—, —CH=CF—, —CF=CH—, —CH$_2$CH$_2$—, —CF$_2$CF$_2$—,

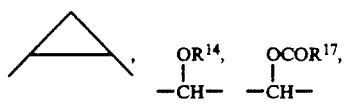

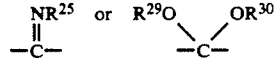

Y is O or S;
Z is O, NR$^{11}$, or S;
m is 1 to 5;
n is 1 to 10;
p is 0 to 3;
q is 2 to 3;
r is 0 to 2;

s is 0 to 5;

t is 0 or 1;

or a pharmaceutically acceptable salt thereof; provided that:

(1) the $R^1$ group is not in the ortho position;

(2) when $R^1$ is

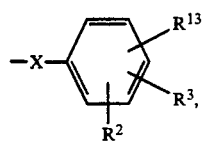

X is a single bond, and $R^{13}$ is $CO_2H$, or

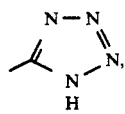

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

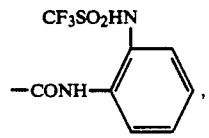

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is 4—$CO_2H$ or a salt thereof, $R^6$ cannot be S-alkyl;

(5) when $R^1$ is 4—$CO_2H$ or a salt thereof, the substituent on the 4-position of the imidazole cannot be $CH_2OH$, $CH_2OCOCH_3$, or $CH_2CO_2H$;

(6) when $R^1$ is

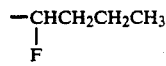

$R^6$ is not methoxybenzyl;

(7) the $R^6$ group is not $$-\underset{F}{\overset{}{C}}HCH_2CH_2CH_3$$

or $CH_2OH$.

* * * * *